(12) United States Patent
Plouhar et al.

(10) Patent No.: US 8,012,205 B2
(45) Date of Patent: Sep. 6, 2011

(54) CARTILAGE REPAIR AND REGENERATION DEVICE

(75) Inventors: Pamela Lynn Plouhar, South Bend, IN (US); Prasanna Malaviya, Ft. Wayne, IN (US); Herbert Eugene Schwartz, Ft. Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 214 days.

(21) Appl. No.: 10/195,606

(22) Filed: Jul. 15, 2002

(65) Prior Publication Data

US 2003/0033022 A1    Feb. 13, 2003

Related U.S. Application Data

(60) Provisional application No. 60/388,724, filed on Jun. 14, 2002, provisional application No. 60/305,786, filed on Jul. 16, 2001.

(51) Int. Cl.
    *A61F 2/08*    (2006.01)
(52) U.S. Cl. .................... 623/13.17; 623/23.63
(58) Field of Classification Search ............... 623/13.17, 623/23.63
    See application file for complete search history.

(56) References Cited

U.S. PATENT DOCUMENTS

| | | | |
|---|---|---|---|
| 3,272,204 A * | 9/1966 | Artandi et al. | 606/151 |
| 3,562,820 A | 2/1971 | Braun | |
| 4,105,034 A * | 8/1978 | Shalaby et al. | 606/230 |
| 4,130,639 A * | 12/1978 | Shalaby et al. | 514/169 |
| 4,140,678 A * | 2/1979 | Shalaby et al. | 525/437 |
| 4,141,087 A * | 2/1979 | Shalaby et al. | 606/230 |
| 4,205,399 A * | 6/1980 | Shalaby et al. | 623/1.38 |
| 4,208,511 A * | 6/1980 | Shalaby et al. | 528/272 |
| 4,352,463 A * | 10/1982 | Baker | 239/663 |
| 4,400,833 A | 8/1983 | Kurland | |
| 4,418,691 A * | 12/1983 | Yannas et al. | 424/548 |
| 4,610,397 A * | 9/1986 | Fischer et al. | 241/86 |
| 4,642,120 A | 2/1987 | Nevo et al. | |
| 4,669,473 A * | 6/1987 | Richards et al. | 606/215 |
| 4,703,108 A * | 10/1987 | Silver et al. | 530/356 |
| 4,705,040 A * | 11/1987 | Mueller et al. | 606/108 |
| 4,741,330 A * | 5/1988 | Hayhurst | 606/144 |
| 4,750,492 A * | 6/1988 | Jacobs | 606/230 |
| 4,846,835 A * | 7/1989 | Grande | 128/898 |
| 4,873,976 A | 10/1989 | Schreiber | |
| 4,880,429 A | 11/1989 | Stone | |
| 4,902,508 A | 2/1990 | Badylak et al. | |
| 4,919,667 A | 4/1990 | Richmond | |
| 4,956,178 A | 9/1990 | Badylak et al. | |
| 4,956,179 A * | 9/1990 | Bamberg et al. | 424/114 |
| 4,976,715 A * | 12/1990 | Bays et al. | 606/77 |
| 5,007,934 A | 4/1991 | Stone | |

(Continued)

FOREIGN PATENT DOCUMENTS

EP    0 446 105 A2    1/1992

(Continued)

OTHER PUBLICATIONS

English translation of JP-11319068-A.*

(Continued)

*Primary Examiner* — Paul Prebilic

(57) ABSTRACT

A cartilage repair device comprises a scaffold, for example a naturally occurring extracellular matrix material, and a biological lubricant. The biological lubricant is applied to the naturally occurring extracellular matrix material.

1 Claim, 5 Drawing Sheets

U.S. PATENT DOCUMENTS

| | | | |
|---|---|---|---|
| 5,061,286 A * | 10/1991 | Lyle | 623/23.63 |
| 5,102,421 A * | 4/1992 | Anspach, Jr. | 606/232 |
| 5,108,438 A | 4/1992 | Stone | |
| 5,128,326 A | 7/1992 | Balazs et al. | |
| RE34,021 E * | 8/1992 | Mueller et al. | 604/533 |
| 5,158,573 A | 10/1992 | Berg | |
| 5,236,431 A | 8/1993 | Gogolewski et al. | |
| 5,246,441 A | 9/1993 | Ross et al. | |
| 5,258,015 A * | 11/1993 | Li et al. | 606/232 |
| 5,269,809 A * | 12/1993 | Hayhurst et al. | 606/232 |
| 5,275,826 A | 1/1994 | Badylak et al. | |
| 5,281,422 A | 1/1994 | Badylak et al. | |
| 5,306,311 A | 4/1994 | Stone et al. | |
| 5,320,633 A | 6/1994 | Allen et al. | |
| 5,350,583 A * | 9/1994 | Yoshizato et al. | 623/15.12 |
| 5,352,463 A | 10/1994 | Badylak et al. | |
| 5,372,821 A | 12/1994 | Badylak et al. | |
| 5,374,268 A | 12/1994 | Sander | |
| 5,376,118 A * | 12/1994 | Kaplan et al. | 623/23.72 |
| 5,380,334 A | 1/1995 | Torrier et al. | |
| 5,445,833 A | 8/1995 | Badylak et al. | |
| 5,447,940 A * | 9/1995 | Harvey et al. | 514/310 |
| 5,460,962 A | 10/1995 | Kemp | |
| 5,464,929 A * | 11/1995 | Bezwada et al. | 528/361 |
| 5,479,033 A | 12/1995 | Baca et al. | |
| 5,514,181 A * | 5/1996 | Light et al. | 623/13.18 |
| 5,516,533 A | 5/1996 | Badylak et al. | |
| 5,520,691 A * | 5/1996 | Branch | 606/72 |
| 5,545,178 A * | 8/1996 | Kensey et al. | 606/213 |
| 5,545,222 A * | 8/1996 | Bonutti | 128/898 |
| 5,554,389 A | 9/1996 | Badylak et al. | |
| 5,569,252 A | 10/1996 | Justin et al. | |
| 5,573,784 A | 11/1996 | Badylak et al. | |
| 5,591,234 A | 1/1997 | Kirsch | |
| 5,593,441 A | 1/1997 | Lichtenstein et al. | |
| 5,595,621 A * | 1/1997 | Light et al. | 156/80 |
| 5,595,751 A * | 1/1997 | Bezwada et al. | 424/422 |
| 5,597,579 A * | 1/1997 | Bezwada et al. | 424/426 |
| 5,601,558 A | 2/1997 | Torrie et al. | |
| 5,607,687 A * | 3/1997 | Bezwada et al. | 424/426 |
| 5,618,552 A * | 4/1997 | Bezwada et al. | 424/426 |
| 5,620,698 A * | 4/1997 | Bezwada et al. | 424/426 |
| 5,626,614 A * | 5/1997 | Hart | 606/232 |
| 5,630,824 A * | 5/1997 | Hart | 606/139 |
| 5,632,745 A | 5/1997 | Schwartz | |
| 5,641,518 A | 6/1997 | Badylak et al. | |
| 5,645,850 A * | 7/1997 | Bezwada et al. | 424/426 |
| 5,645,860 A | 7/1997 | Knapp, Jr. et al. | |
| 5,648,088 A * | 7/1997 | Bezwada et al. | 424/426 |
| 5,660,225 A * | 8/1997 | Saffran | 128/898 |
| 5,668,288 A | 9/1997 | Storey et al. | |
| 5,669,912 A | 9/1997 | Spetzler | |
| 5,677,355 A | 10/1997 | Shalaby et al. | |
| 5,681,353 A | 10/1997 | Li et al. | |
| 5,693,085 A * | 12/1997 | Buirge et al. | 623/1.13 |
| 5,695,998 A | 12/1997 | Badylak et al. | |
| 5,698,213 A * | 12/1997 | Jamiolkowski et al. | 424/426 |
| 5,700,583 A * | 12/1997 | Jamiolkowski et al. | 428/482 |
| 5,702,462 A | 12/1997 | Oberlander | |
| 5,711,969 A | 1/1998 | Patel et al. | |
| 5,725,556 A * | 3/1998 | Moser et al. | 606/232 |
| 5,730,933 A | 3/1998 | Peterson | |
| 5,733,337 A | 3/1998 | Carr, Jr. et al. | |
| 5,733,868 A | 3/1998 | Peterson et al. | |
| 5,735,897 A * | 4/1998 | Buirge | 623/1.15 |
| 5,735,903 A | 4/1998 | Li et al. | |
| 5,736,372 A * | 4/1998 | Vacanti et al. | 435/180 |
| 5,753,267 A | 5/1998 | Badylak et al. | |
| 5,755,791 A | 5/1998 | Whitson et al. | |
| 5,759,190 A | 6/1998 | Vibe-Hansen et al. | |
| 5,759,205 A | 6/1998 | Valentini | |
| 5,759,208 A * | 6/1998 | Zhen et al. | 8/137 |
| 5,762,966 A | 6/1998 | Knapp et al. | |
| 5,769,899 A | 6/1998 | Schwartz et al. | |
| 5,773,577 A * | 6/1998 | Cappello | 530/350 |
| 5,782,835 A * | 7/1998 | Hart et al. | 606/79 |
| 5,788,625 A * | 8/1998 | Plouhar et al. | 600/36 |
| 5,795,353 A | 8/1998 | Felt | |
| 5,800,537 A * | 9/1998 | Bell | 424/93.1 |
| 5,817,095 A * | 10/1998 | Smith | 606/79 |
| 5,830,708 A * | 11/1998 | Naughton | 435/70.1 |
| 5,834,232 A * | 11/1998 | Bishop et al. | 435/68.1 |
| 5,842,477 A | 12/1998 | Naughton et al. | |
| 5,847,012 A | 12/1998 | Shalaby et al. | |
| 5,855,610 A * | 1/1999 | Vacanti et al. | 623/2.13 |
| 5,855,613 A | 1/1999 | Antanavich et al. | |
| 5,855,619 A | 1/1999 | Caplan et al. | |
| 5,859,150 A * | 1/1999 | Jamiolkowski et al. | 525/437 |
| 5,861,004 A * | 1/1999 | Kensey et al. | 606/213 |
| 5,863,551 A * | 1/1999 | Woerly | 424/423 |
| 5,866,165 A * | 2/1999 | Liu et al. | 424/486 |
| 5,866,414 A | 2/1999 | Badylak et al. | |
| 5,885,619 A | 3/1999 | Patel et al. | |
| 5,891,558 A * | 4/1999 | Bell et al. | 428/218 |
| 5,899,939 A * | 5/1999 | Boyce et al. | 623/16.11 |
| 5,906,997 A * | 5/1999 | Schwartz et al. | 514/781 |
| 5,916,265 A | 6/1999 | Hu | |
| 5,922,028 A | 7/1999 | Plouhar et al. | |
| 5,939,323 A * | 8/1999 | Valentini et al. | 435/395 |
| 5,948,429 A | 9/1999 | Bell et al. | |
| 5,954,723 A | 9/1999 | Spetzler | |
| 5,954,747 A | 9/1999 | Clark | |
| 5,955,100 A | 9/1999 | Bosslet et al. | |
| 5,958,874 A | 9/1999 | Clark et al. | |
| 5,968,096 A | 10/1999 | Whitson et al. | |
| 5,969,020 A | 10/1999 | Shalaby et al. | |
| 5,971,987 A | 10/1999 | Huxel et al. | |
| 5,980,524 A | 11/1999 | Justin et al. | |
| 5,981,825 A * | 11/1999 | Brekke | 623/11.11 |
| 5,989,269 A | 11/1999 | Vibe-Hansen et al. | |
| 5,989,280 A * | 11/1999 | Euteneuer et al. | 623/1.1 |
| 5,993,475 A | 11/1999 | Lin et al. | |
| 5,993,844 A | 11/1999 | Abraham et al. | |
| 5,997,575 A | 12/1999 | Whitson et al. | |
| 6,010,525 A * | 1/2000 | Bonutti et al. | 606/232 |
| 6,010,692 A * | 1/2000 | Goldberg et al. | 424/78.06 |
| 6,017,301 A * | 1/2000 | Schwartz et al. | 514/781 |
| 6,017,348 A | 1/2000 | Hart et al. | |
| 6,027,744 A | 2/2000 | Vacanti et al. | |
| 6,034,140 A * | 3/2000 | Schwartz et al. | 514/781 |
| 6,042,610 A | 3/2000 | Li et al. | |
| 6,051,750 A | 4/2000 | Bell | |
| 6,056,752 A | 5/2000 | Roger | |
| 6,056,777 A | 5/2000 | McDowell | |
| 6,056,778 A | 5/2000 | Grafton et al. | |
| 6,060,640 A | 5/2000 | Pauley et al. | |
| 6,066,160 A * | 5/2000 | Colvin et al. | 606/232 |
| 6,068,648 A | 5/2000 | Cole et al. | |
| 6,077,989 A * | 6/2000 | Kandel et al. | 623/13.17 |
| 6,080,194 A | 6/2000 | Pachence et al. | |
| 6,093,201 A | 7/2000 | Cooper et al. | |
| 6,096,347 A | 8/2000 | Geddes et al. | |
| 6,099,567 A | 8/2000 | Badylak et al. | |
| 6,110,212 A * | 8/2000 | Gregory | 623/23.72 |
| 6,126,686 A | 10/2000 | Badylak et al. | |
| 6,133,325 A * | 10/2000 | Schwartz et al. | 514/781 |
| 6,146,385 A | 11/2000 | Torrie et al. | |
| 6,152,935 A | 11/2000 | Kammerer et al. | |
| 6,153,292 A | 11/2000 | Bell et al. | |
| 6,156,044 A | 12/2000 | Kammerer et al. | |
| 6,165,225 A * | 12/2000 | Antanavich et al. | 623/23.72 |
| 6,171,344 B1 | 1/2001 | Atala | |
| 6,176,880 B1 | 1/2001 | Plouhar et al. | |
| 6,179,840 B1 | 1/2001 | Bowman | |
| 6,179,872 B1 | 1/2001 | Bell et al. | |
| 6,187,039 B1 | 2/2001 | Hiles et al. | |
| 6,197,296 B1 * | 3/2001 | Davies et al. | 424/93.7 |
| 6,206,931 B1 | 3/2001 | Cook et al. | |
| 6,214,048 B1 * | 4/2001 | Ito et al. | 623/16.11 |
| 6,214,049 B1 | 4/2001 | Gayer et al. | |
| 6,224,892 B1 | 5/2001 | Searle | |
| 6,235,057 B1 | 5/2001 | Roger et al. | |
| 6,242,247 B1 | 6/2001 | Rieser et al. | |
| 6,251,143 B1 | 6/2001 | Schwartz et al. | |
| 6,251,876 B1 | 6/2001 | Bellini et al. | |
| 6,258,124 B1 * | 7/2001 | Darois et al. | 623/14.13 |
| 6,264,702 B1 * | 7/2001 | Ory et al. | 623/23.75 |

| | | | |
|---|---|---|---|
| 6,265,333 B1 * | 7/2001 | Dzenis et al. ............... 442/346 |
| 6,267,957 B1 * | 7/2001 | Green et al. ................ 424/94.5 |
| 6,270,530 B1 * | 8/2001 | Eldridge et al. ........... 623/23.74 |
| 6,273,893 B1 | 8/2001 | McAllen, III et al. |
| 6,280,473 B1 * | 8/2001 | Lemperle et al. ........... 623/16.11 |
| 6,280,474 B1 * | 8/2001 | Cassidy et al. ............. 623/16.11 |
| 6,283,980 B1 | 9/2001 | Vibe-Hansen et al. |
| 6,288,043 B1 | 9/2001 | Spiro et al. |
| 6,290,711 B1 * | 9/2001 | Caspari et al. ............... 606/232 |
| 6,293,961 B2 | 9/2001 | Schwartz et al. |
| 6,294,041 B1 * | 9/2001 | Boyce et al. ............... 156/275.5 |
| 6,299,905 B1 * | 10/2001 | Peterson et al. .............. 424/486 |
| 6,306,156 B1 | 10/2001 | Clark |
| 6,306,159 B1 | 10/2001 | Schwartz et al. |
| 6,306,177 B1 | 10/2001 | Felt et al. |
| 6,319,258 B1 | 11/2001 | McAllen, III et al. |
| 6,319,271 B1 | 11/2001 | Schwartz et al. |
| 6,326,025 B1 | 12/2001 | Sigler et al. |
| 6,333,029 B1 | 12/2001 | Vyakarnam et al. |
| 6,334,872 B1 | 1/2002 | Termin et al. |
| 6,355,699 B1 | 3/2002 | Vyakarnam et al. |
| 6,358,284 B1 * | 3/2002 | Fearnot et al. ............. 623/23.72 |
| 6,364,884 B1 | 4/2002 | Bowman et al. |
| 6,371,958 B1 | 4/2002 | Overaker |
| 6,373,221 B1 * | 4/2002 | Koike et al. .................. 320/108 |
| 6,379,367 B1 | 4/2002 | Vibe-Hansen et al. |
| 6,379,710 B1 | 4/2002 | Badylak |
| 6,383,221 B1 | 5/2002 | Scarborough et al. |
| 6,387,693 B2 * | 5/2002 | Rieser et al. ................ 435/297.1 |
| 6,402,766 B2 * | 6/2002 | Bowman et al. .............. 606/151 |
| 6,409,764 B1 | 6/2002 | White et al. |
| 6,423,073 B2 * | 7/2002 | Bowman ...................... 606/104 |
| 6,436,110 B2 * | 8/2002 | Bowman et al. .............. 606/151 |
| 6,440,444 B2 * | 8/2002 | Boyce et al. ................. 424/422 |
| 6,447,517 B1 * | 9/2002 | Bowman ........................ 606/75 |
| 6,451,032 B1 * | 9/2002 | Ory et al. ..................... 606/151 |
| 6,458,158 B1 * | 10/2002 | Anderson et al. ........... 623/16.11 |
| 6,458,383 B2 * | 10/2002 | Chen et al. .................... 424/451 |
| 6,464,729 B1 * | 10/2002 | Kandel ....................... 623/23.63 |
| 6,497,650 B1 * | 12/2002 | Nicolo ........................... 600/37 |
| 6,497,707 B1 * | 12/2002 | Bowman et al. ................ 606/75 |
| 6,508,821 B1 * | 1/2003 | Schwartz et al. .............. 606/148 |
| 6,517,564 B1 * | 2/2003 | Grafton et al. ................ 606/213 |
| 6,566,345 B2 * | 5/2003 | Miller et al. .................... 514/54 |
| 6,572,650 B1 * | 6/2003 | Abraham et al. ............. 623/1.38 |
| 6,579,978 B1 * | 6/2003 | Renier et al. .................... 536/53 |
| 6,592,623 B1 * | 7/2003 | Bowlin et al. ............... 623/14.13 |
| 6,638,312 B2 * | 10/2003 | Plouhar et al. .............. 623/23.72 |
| 6,652,872 B2 * | 11/2003 | Nevo et al. .................... 424/423 |
| 6,666,892 B2 * | 12/2003 | Hiles et al. .................. 623/23.72 |
| 6,692,499 B2 * | 2/2004 | Tormala et al. ................ 606/72 |
| 6,812,221 B2 * | 11/2004 | McKeehan et al. ............. 514/56 |
| 6,840,962 B1 * | 1/2005 | Vacanti et al. .............. 623/23.76 |
| 6,869,938 B1 * | 3/2005 | Schwartz et al. ............... 514/57 |
| 6,989,034 B2 * | 1/2006 | Hammer et al. ............ 623/23.72 |
| 7,121,999 B2 * | 10/2006 | Abraham et al. ............... 600/36 |
| 7,361,195 B2 * | 4/2008 | Schwartz et al. ........... 623/23.63 |
| 7,838,630 B2 * | 11/2010 | Murray et al. ............... 530/356 |
| 2001/0002446 A1 * | 5/2001 | Plouhar et al. .............. 623/14.12 |
| 2001/0023373 A1 * | 9/2001 | Plouhar et al. .............. 623/23.72 |
| 2001/0024658 A1 * | 9/2001 | Chen et al. .................... 424/452 |
| 2001/0039455 A1 * | 11/2001 | Simon et al. ................ 623/23.51 |
| 2001/0043943 A1 * | 11/2001 | Coffey ......................... 424/447 |
| 2002/0019649 A1 | 2/2002 | Sikora et al. |
| 2002/0031551 A1 * | 3/2002 | Peterson et al. .............. 424/486 |
| 2002/0034533 A1 * | 3/2002 | Peterson et al. .............. 424/423 |
| 2002/0038151 A1 * | 3/2002 | Plouhar et al. .............. 623/23.72 |
| 2002/0048595 A1 | 4/2002 | Geistlich et al. |
| 2002/0052628 A1 * | 5/2002 | Bowman ...................... 606/232 |
| 2002/0055783 A1 * | 5/2002 | Tallarida et al. ............. 623/20.14 |
| 2002/0095157 A1 * | 7/2002 | Bowman ........................ 606/75 |
| 2002/0099448 A1 | 7/2002 | Hiles |
| 2002/0103542 A1 * | 8/2002 | Bilbo ........................... 623/23.72 |
| 2002/0165611 A1 * | 11/2002 | Enzerink et al. ............ 623/13.11 |
| 2002/0169465 A1 * | 11/2002 | Bowman et al. .............. 606/151 |
| 2002/0173806 A1 | 11/2002 | Giannetti et al. |
| 2003/0014126 A1 * | 1/2003 | Patel et al. .................. 623/23.72 |
| 2003/0021827 A1 * | 1/2003 | Malaviya et al. ............. 424/424 |
| 2003/0023316 A1 * | 1/2003 | Brown et al. ............... 623/23.72 |
| 2003/0032961 A1 * | 2/2003 | Pelo et al. ....................... 606/72 |
| 2003/0033021 A1 * | 2/2003 | Plouhar et al. .............. 623/23.57 |
| 2003/0033022 A1 * | 2/2003 | Plouhar et al. .............. 623/23.57 |
| 2003/0036797 A1 * | 2/2003 | Malaviya et al. ........... 623/14.12 |
| 2003/0036801 A1 * | 2/2003 | Schwartz et al. ........... 623/23.63 |
| 2003/0044444 A1 * | 3/2003 | Malaviya et al. .............. 424/423 |
| 2003/0049299 A1 * | 3/2003 | Malaviya et al. .............. 424/423 |
| 2003/0078617 A1 * | 4/2003 | Schwartz et al. .............. 606/230 |
| 2003/0212447 A1 * | 11/2003 | Euteneuer et al. .............. 623/1.2 |
| 2003/0236573 A1 * | 12/2003 | Evans et al. ................. 623/23.58 |
| 2004/0059431 A1 * | 3/2004 | Plouhar et al. .............. 623/23.74 |
| 2004/0143344 A1 * | 7/2004 | Malaviya et al. ............ 623/23.72 |
| 2004/0166169 A1 * | 8/2004 | Malaviya et al. .............. 424/551 |
| 2004/0220574 A1 * | 11/2004 | Pelo et al. ....................... 606/73 |
| 2005/0027307 A1 * | 2/2005 | Schwartz et al. .............. 606/151 |
| 2005/0249771 A1 * | 11/2005 | Malaviya et al. .............. 424/423 |
| 2005/0249772 A1 * | 11/2005 | Malaviya et al. .............. 424/423 |
| 2006/0155384 A1 * | 7/2006 | Ellingsen et al. ........... 623/23.53 |

FOREIGN PATENT DOCUMENTS

| | | |
|---|---|---|
| EP | 0552593 | 7/1993 |
| EP | 0591991 A2 | 4/1994 |
| EP | 0632999 A1 | 11/1995 |
| EP | 0 734 736 A1 | 10/1996 |
| EP | 1593400 A1 | 11/2005 |
| GB | 2215209 A | 9/1989 |
| JP | 11319068 A | 11/1999 |
| WO | WO 90/09769 | 9/1990 |
| WO | 9315721 | 8/1993 |
| WO | WO 94/11008 | 5/1994 |
| WO | WO 95/05083 | 2/1995 |
| WO | WO 95/22301 | 8/1995 |
| WO | WO 95/06439 | 9/1995 |
| WO | WO 95/32623 | 12/1995 |
| WO | WO 96/24661 | 8/1996 |
| WO | WO 97/05193 | 2/1997 |
| WO | 9715195 | 5/1997 |
| WO | WO 97/37613 | 10/1997 |
| WO | WO 98/06445 | 2/1998 |
| WO | 9822154 | 5/1998 |
| WO | WO 98/22158 A2 | 5/1998 |
| WO | WO 98/22158 A3 | 5/1998 |
| WO | WO 98/30167 | 7/1998 |
| WO | WO 98/34569 | 8/1998 |
| WO | WO 98/40111 | 9/1998 |
| WO | WO 99/03979 | 1/1999 |
| WO | 9919005 | 4/1999 |
| WO | WO 99/43786 | 9/1999 |
| WO | WO 99/47188 | 9/1999 |
| WO | WO 99/62427 A1 * | 12/1999 |
| WO | WO 00/15765 | 3/2000 |
| WO | WO 00/16822 | 3/2000 |
| WO | WO 00/24437 A2 | 5/2000 |
| WO | WO 00/24437 A3 | 5/2000 |
| WO | WO 00/32250 | 6/2000 |
| WO | WO 00/48550 | 8/2000 |
| WO | WO 00/72782 | 12/2000 |
| WO | WO 01/19423 | 3/2001 |
| WO | WO 01/39694 A2 | 6/2001 |
| WO | WO 01/39694 A3 | 6/2001 |
| WO | WO 01/45765 | 6/2001 |
| WO | WO 01/66159 | 9/2001 |
| WO | WO 02/22184 | 3/2002 |
| WO | WO 03/007784 | 1/2003 |
| WO | WO-03/007788 A2 * | 1/2003 |
| WO | WO 03/007790 | 1/2003 |

OTHER PUBLICATIONS

Wikipedia online definition of "hyaluronic acid" at http://en.wikipedia.org/wiki/Hyaluronate.*
Michael W. King, Ph.D, online article entitled "Extracellular Matrix (ECM)", at http://web.indstate.edu/thcme/mwking/extracellularmatrix.html.*
On-line Medical Dictionary definition for "glucosaminoglycan."*
On-line Medical Dictionary definition for "hyaluronic acid."*
Provisional Application to Organogenesis filed Sep. 18, 2000 which is relied upon for priority in publication US 2002/0103542.*

Biology-Online defintion of "Submucosa" located at http://www.biology-online.org/dictionary/Submucosa.*
Biology-Online definition of "Connective Tissue" located at http://www.biology-online.org/dictionary/Connective_tissues.*
Biology-Online definition of "Hyaluronic acid" located at http://www.biology-online.org/dictionary/Hyaluronic_acid.*
Hiles et al., "Mechanical properties of xenogeneic small-intestinal submucosa when used as an aortic graft in the dog", *Journal of Biomedical Materials Research*, vol. 29, 883-891, (1995).
Sandusky, et al., "Healing Comparison of Small Intestine Submucosa and ePTFE Grafts in the Canine Carotid Artery", *J. Surg. Res.*, 58:415-420, (1995).
Knapp, et al., "Biocompatibility of Small-Intestine Submucosa in Urinary Tract as Augmentation Cystoplasty Graft and Injectable Suspension", *J Endourology*, 8:125-130, (1994).
Kropp et al., "Regenerative Bladder Augmentation: A Review of the Initial Preclinical Studies with Porcine Small Intestinal Submucosa", *Muscle, Matrix, and Bladder Function*, Plenum Press, New York, (1995).
Kropp et al., "Experimental Assessment of Small Intestinal Submucosa as a Bladder Wall Substitute", *Urology* 446:396-400, (1995).
Vaught et al., "Detrusor Regeneration in the Rat Using Porcine Small Intestinal Submucosa Grafts: Functional Innervation and Receptor Expression", *J. Urol.*, 155:374-378, (1996).
Kropp et al, Characterization of Small Intestinal Submucosa Regenerated Canine Detrusor: Assessment of Reinnervation, In Vitro Compliance and contractility, *J. of Urol.*156:599-607, (1996).
Kropp et al., "Regenerative Urinary Bladder Augmentation Using Small Intestinal Submucosa: Urodynamic and Histopathologic Assessment in Long-Term Canine Bladder Augmentations", *Journal of Urology*, 155:2098-2104, (1996).
Aiken et al., "Small Intestinal Submucosa as an Intra-Articular Ligamentous Graft Material: A Pilot Study in Dogs", *Vet Comp Orthopedics Traumatology*, 7:124-128, (1994).
Badylak et al., "The Use of Xenogeneic Small Intestinal Submucosa as a Biomaterial for Achille's Tendon Repair in a dog model", *J Biomed Materials*, 29:977-985, (1995).
Hodde et al., "The Effect of Range of Motion Upon Remodeling of Small Intestinal Submucosa (SIS) when used as an Achilles Tendon Repair Material in the Rabbit", *Tissue Engineering* 3, 1:27-37, (1997).
Ferrand et al., "Directional Porosity of Porcine Small-Intestinal Submucosa", *J Biomed Materials Res*, 27:1235-1241, (1993).
Hiles et al., "Porosity of Porcine Small-Intestinal Submucosa for use as a Vascular Graft", *J Biomed Materials Res*, 27: 139-144, (1993).
Hodde et al., "Glycosaminoglycan Content of Small Intestinal Submucosa: A Bioscaffold for Tissue Replacement", *Tissue Engineering*, 2:3, 209-217, (1996).
Prevel et al., "Small Intestinal Submucosa: Utilization for Repair of Rodent Abdominal Wall Defects", *Ann Plast Surg*, 35:374-380, (1995).
Clarke et al., "Intestine Submucosa and Polypropylene Mesh for Abdominal Wall Repair in Dogs", *J Surg Res*, 60:107-114, (1996).
Prevel et al., "Small Intestinal Submucosa: Utilization as a Wound Dressing in Full-Thickness Rodent Wounds", *Ann Plast Surg.* 35:381-388, (1995).
Cobb et al., "Histology after Dural Grafting with Small Intestinal Submucosa", *Surgical Neurology*, 46: 389-394, (1996).
Cobb et al., "Porcine Small Intestinal Submucosa as a Dural Substitute", *Surgical Neurology*, 51:99-104, (1999).
Voytik-Harbin et al., "Application and Evaluation of the AlamarBlue Assay for Cell Growth and Survival of Fibroblasts", *Journal of Immunological Methods. In Vitro Cell Bio-Animal,* 34: 2399-246, (1998).
Suckow, M.A., "Enhanced Bone Regeneration Using Porcine Small Intestinal Submucosa", *J. Invest Surg*, 12: 277, (1999).
Badylak, S., et al., "Naturally Occurring Extracellular Matrix as a Scaffold for Musculoskeletal Repair", *Clin Orthop*, 3675:S333-S3433, (1999).
Cook, J.L. et al., "Induction of Meniscal Regeneration in Dogs Using a Novel Biomaterial", *Am J Sports Med*, 27: 658, (1999).

Dejardin, L.M. et al., "Use of small intestinal submucosal implants for regeneration of large fascial defects: an experimental study in dogs", J Biomed Mater Res, 46:203-211, (1999).
Sacks, M.S., et al., "Quantification of the fiber architecture and biaxial mechanical behavior of porcine intestinal submucosa", *J Biomed Mater Res*, 46:1-10, (1999).
COOK® News Releases, "COOK® Introduces Innovative Surgisis™ Soft Tissue Repair Biomaterial", (May 21, 2000).
COOK® News Releases, "COOK® Oasis™ Wound Dressing Biomaterial From COOK® Remodels Partial Thickness Skin Injuries", (Dec. 23, 1999).
COOK® News Releases, "Cook Incorporated Forms Dedicated Tissue Engineered Products Group", (Feb. 16, 2000).
COOK® News Releases, "FDA Clears Oasis™ Wound Dressing Biomaterial From COOK® for Full-Thickness Skin Injuries", (Jan. 24, 2000).
Klootwyk, et al., "The Use of Xenographic SIS as a Biomaterial for Achilles Tendon Repair in Dogs," First SIS Symposium, Dec. 1996, USA.
Lenz, et al., "SIS as an ACL Replacement in Dogs and Goats," First Symposium, Dec. 1996, USA.
Cook, et al., "Comparison of SIS Cancellous Bone as Substrates for Three-Dimensional Culture of Canine Articular Chondrocytes," First SIS Symposium, Dec. 1996, USA.
Badylak, et al., "Different Configurations of Small Intestinal Submucosa as a Biomaterial for Achilles Tendon Repair in a Dog Model," First SIS Symposium, Dec. 1996, USA.
Voytik-Harbin & Badylak, "Induction of Osteogenic Activity by Small Intestinal Submucosa in Rat Calvaria Non-union Defects," First SIS Symposium, Dec. 1996, USA.
Kandel, et al., "SIS and Reconstituted Cartilage and its Use in Joint Resurfacing of Focal Defects in Rabbits," First SIS Symposium, Dec. 1996, USA.
Tullius, et al., "Differential Permeabilty of SIS," First SIS Symposium, Dec. 1996, USA.
Obermiller, et al., "Suture Retention Strength of SIS," First SIS Symposium, Dec. 1996, USA.
Shelton, et al., "Repair of the Canine Medial Meniscus using SIS: A Feasibility Study," Second SIS Symposium, Dec. 1998, USA.
Cook, et al., "Meniscal Regeneration in dogs Using Grafts of SIS," Second SIS Symposium, Dec. 1998, USA.
Welch, et al., "Healing of Canine Meniscal Defect with Small Intestinal Submucosa Implants," Dec. 1998, USA.
Solchaga, et al., "SIS as Delivery Vehicle for Mesenchymal Progenitor Cells," Dec. 1998, USA.
Paulino, et al., "The Use of an SIS-PGA Composite Graft for Repair of Cartilage Defect," Dec. 1998, USA.
Toombs and May, "Clinical Follow-Up of Three Canine ACL Reconstructions Using an SIS ACL Device," Dec. 1998, USA.
Tomasek and Gifford, "Small Intestinal Submucosa Matrix Regulates the Differentiation of Myofibroblasts," Third SIS Symposium, Nov. 2000, USA.
Cook, et al., "Tissue Engineering for Meniscal Repair Using SIS," Third SIS Symposium, Nov. 2000, USA.
Lifrak, et al., "Enhanced Repair of Goat Meniscal Defects Using Porcine Small Intestinal Submucosa (SIS)," Third SIS Symposium, Nov. 2000, USA.
Hoffman, "SIS Disc Replacement for the Temporomandibular Joint," Third SIS Symposium, Nov. 2000, USA.
Kaeding, "Use of SIS in the Surgical Treatment of Chronic Symptomatic Patella Tendinosis," Third SIS Symposium, Nov. 2000, USA.
Tomczak and Kaeding, "Use of SIS in the Surgical Treatment of Tendinosis About the Foot and Ankle," Third SIS Sympsosium, Nov. 2000, USA.
Moore, et al., "Bridging Segmental Defects in Long Bones With Intramedullary Tubes and Periosteal Sleeves Made From Small Intestinal Submucosa (SIS)," Third SIS Symposium, Nov. 2000, USA.
Wang, et al., "Small Intestinal Submucosa Enhances Healing of Medical Collateral Ligament in a Rabbit Model," Third SIS Symposium, Nov. 2000, USA.
Ojha, et al., "PGA-PIIa Versus Small Intestinal Submucosa (SIS): A Comparison of Neo-Cartilage Grown From Two Scaffold Materials," Third SIS Symposium, Nov. 2000, USA.

Wiklerson, "Use of the Porcine Small Intestine Submucosal Tissue Graft and Repair of Rotator Cuff Tears," Third SIS Symposium, Nov. 2000, USA.
"Small Intestinal Submucosa," Third SIS Symposium, Nov. 2000, USA.
"Current Clinical Applications of SIS," Third SIS Symposium, Nov. 2000, USA.
Hodde, et al., "Glycosaminoglycan Content of Small Intestinal Submucosa: A Potential for GAG-Growth Interactions in SIS-Mediated Healing", First Symposium, Dec. 1996, USA.
Friess, "Collagen in drug delivery and tissue engineering", Advanced Drug Delivery Reviews, vol. 55, No. 12, 2003, pp. 1529-1530.
Olsen et al., "Recombinant collagen and gelatin for drug delivery", Advanced Drug Delivery Reviews, vol. 55, No. 12, 2003, pp. 1547-1567.
Aigner et al., "Collagens-major component of the physiological cartilage matrix, major target of cartilage degeneration, major tool in cartilage repair", Advanced Drug Delivery Reviews, vol. 55, No. 12, 2003, pp. 1569-1593.
Geiger el al., "Collagen sponges for bone regeneration with rhBMP-2", Advanced Drug Delivery Reviews, vol. 55, No. 12, 2003, pp. 1613-1629.
Ruszczak et al., "Collagen as a carrier for on-site delivery of antibacterial drugs", Advanced Drug Delivery Reviews, vol. 55, No. 12, 2003, pp. 1679-1698.
O'Grady et al., "Global regulatory registration requirements for collagen-based combination products: points to consider", Advanced Drug Delivery Reviews, vol. 55, No. 12, 2003, pp. 1699-1721.
Matthews et al., "Electrospinning of Collagen Type II: A Feasibility Study", Journal of Bioactive and Compatible Polymers, vol. 18, Mar. 2003, pp. 125-134.
Biscarini et al., "Growth of High Vacuum Sublimed Oligomer Thin Films", ACS Polymer Preprints, vol. 37, No. 2, 1996, pp. 618-619.
Biscarini et al., "Morphology and roughness of high-vacuum sublimed oligomer thin films", Thin Solid Films, vol. 439-443, 1996, pp. 284-285.
Biscarini el al., "Scaling Behavior of Anisotropic Organic Thin Films Grown in High-Vacuum", Physical Review Letters, vol. 78, No. 12, Mar. 24, 1997, pp. 2389-2392.
Voytik-Harbin et al., "Identification of Extractable Growth Factors from Small Intestinal Submucosa", Journal of Cellular Biochemistry, vol. 67, 1997, pp. 478-491.
McPherson, Ph.D. et al., "Characterization of Fibronectin Derived from Porcine Small Intestinal Submucosa", Tissue Engineering, vol. 4, No. 1, 1998, pp. 75-83.
Hodde, et al., "Vascular Endothelial Growth Factor in Porcine-Derived Extracellular Matrix", Endothelium, vol. 8(1), 2001, pp. 11-24.
Hodde et al., "Wounds: A Compendium of Clinical Research and Practice", Website: http:www.hmpcommunications.com/WNDS, Printed: Jul. 12, 2005, 7 pgs.
Hurst et al., "Mapping of the distribution of significant proteins and proteoglycans in small intestinal submucosa by fluorescence microscopy", J. Biomater. Sci. Polymer Edn., vol. 12, No. 11, 2001, pp. 1267-1279.
Hodde et al., "Fibronectin peptides mediate HMEC adhesion to porcine-derived extracellular matrix", Biomaterials, vol. 23, 2002, pp. 1841-1848.
Hodde, "Naturally Occurring Scaffolds for Soft Tissue Repair and Regeneration", Tissue Engineering, vol. 8, No. 2, 2002, pp. 295-308.
Allman et al., Xenogeneic Extracellular Matrix Grafts Elicit a Th2-Restricted Immune Response, Transplantation, vol. 71, No. 11, Jun. 15, 2001, pp. 1631-1640.
Krčma, "Nonwoven Textiles", Textile Trade Press, Manchester, England, 1962, 6 pgs.
Answers.com,. Definition of "freeze-dry", Accessed on May 12, 2005, 6 pgs.
Ma et al., "Microtubular architecture of biodegradable polymer scaffolds", J. Biomed. Materials Res., vol. 58, No. 4, 2001, pp. 469-477.
Ma et al., "Biodegradable Polymer Scaffolds with Well-Defined Interconnected Spherical Pore Network", Tissue Engineering, vol. 7, No. 1, 2001, pp. 23-33.

Klawitter et al., "An Evaluation of Bone Growth into Porous High Density Polyethylene", J. Biomed. Materials Res., vol. 10, (1976) pp. 311-323.
White et al., "Biomaterial Aspects of Interpore-200 Porous Hydroxyapatite", Dental Clinics of North America, Reconstructive Implant Surgery and Implant Prosthodontics 1, vol. 30, No. 1, pp. 49-67.
Shors, Coralline Bone Graft Substitutes, Orthopaedic Clinics of North America, Bone Grafting and Bone Graft Substitutes, vol. 30, No. 4, Oct. 1999, pp. 599-613.
Wang, Experimental Study of Osteogenic Activity of Sintered Hydroxyapatite—On the Relationship of Sintering Temperature and Pore Size—, J. Jpn. Orthop. Assoc., vol. 64, 1990, pp. 847-859.
Nehrer et al., "Matrix collagen type and pore size influence behavior of seeded canine chondrocytes", Biomaterials, vol. 18, No. 11, 1997, pp. 769-776.
Salem et al., "Interactions of 3T3 fibroblasts and endothelial with defined pore ffeatures", J. Biomed Materials Res., vol. 61, No. 2, 2002, pp. 212-217.
Definitions of "intertwine" and "twine" , American Heritage Dictionary of the English Language Online, Accessed Sep. 29, 2005, 2 pgs.
How to Cut Meat Products 2001, Urschel Corp., Accessed online at fr.urschel.com/literature/HTCMeat.pdf on Oct. 3, 2005, 8 pgs.
Definitions of "comminute" and "slurry", Dictionary.com; Accessed Sep. 20, 2005, 2 pgs.
P. K. Chu et al., "Plasma-surface modification of biomaterials", Materials Science and Engineering, Reports: A Review Journal, vol. 36, No. 5-6, Mar. 29, 2002, pp. 143-206.
Arnoczky et al., The microvasculature of the meniscus and its response to injury—An experimental study in the dog, Am. J. Sports Med., 1983, 11(3); pp. 131-141.
Fox et al., Trephination of incomplete meniscal tears, Arthroscopy, 1993, 9(4); pp. 451-455.
Arnoczky et al., Meniscal repair using an exogenous fibrin clot—An experimental study of dogs, J. Bone Joint Surg. Am., 1988, 70(8), pp. 1209-1216.
Rodeo, "Arthroscopic meniscal repair with use of the outside-in technique", Instr. Course Lect., 2000, 49, pp. 195-206.
Stollsteimer et al., "Meniscal allograft transplantation: a 1- to 5-year follow-up of 22 patients", Arhroscopy, 2000, 16(4), pp. 343-347.
Rodeo, "Meniscal allografts—where do we stand?", Am. J. Sports Med., 2001, 29(2), pp. 246-261.
Sweigart et al., "Toward tissue engineering of the knee meniscus", Tissue Eng., 2001, 7(2), pp. 111-129.
Boss et al., "Technical innovative: creation of a peripheral vascularized trough to enhance healing in cryopreserved meniscal allograft reconstruction", Knee Surg Sports Traumataol Arthrosc., 2000, 8(3), pp. 159-162.
Siegel et al., "Meniscal allografts", Clin Sports Med., 1993, 12(1), pp. 59-80.
Klompmaker et al., "Meniscal replacement using a porous polymer prosthesis: a preliminary study in the dog.", Biomaterials, 1996, 17(12), pp. 1169-1175.
de Groot et al., "Use of porous polyurethanes for meniscal reconstruction and meniscal protheses", Biomaterials, 1996, 17(2), pp. 163-173.
Spaans et al., "Solvent-free fabrication of micro-porous polyurethane amide and polyurethane-urea scaffolds for repair and replacement of the knee-joint meniscus", Biomaterials, 2000, 21(23), pp. 2453-2460.
Stone et al., "Regeneration of meniscal cartilage with use of a collagen scaffold—Analysis of Preliminary data", J. Bone Joint Surg. Am., 1997, 79(12), pp. 1770-1777.
Rodkey et al., "A clinical study of collagen meniscus implants to restore the injured meniscus", Clin. Orthop., 1999, 49(367 Suppl.), pp. S281-S292.
Merriam-Webster Online Dictionary definitions of "suspension", "suspend", "cohesive", "cohesion", "comminute", "pulverize", "submucosa", and "tissue". Accessed Mar. 30, 2006, 9 pgs.
Resin Technology Group, LLC, "Viscosity chart", http://www.resintechgroup.com/tables/viscosity.html, accessed online Mar. 30, 2006, 1pg.
Definitions from Onelook.com for "trimethylen" and "trimethylene".

J.S. Pieper et al "Preparation and characterization of porous crosslinked collagenous matrices containing bioavallable chondroitin suplhate" Biomaterials 1999, 20: 847-858.

P.B. van Wachem et al. "In vivo biocompatability of carbodiimide-crosslinked collagen matrices: Effects of crosslink density, heparin immobilization, and bFGF loading" J. Biomed. Mater. Res. 2001, 55 (3): 368-378.

Kyumin Whang "A biodegradable polymer scaffold for delivery of osteotropic factors" Biomaterials 2000, 21 (24): 2545-2551.

J.S. Pieper et al. Attachment of glycosaminoglycans to collangenous matrices modulates the tissue response in rats, Biomaterials 2000, 21 (16): 1689-1699.

Kristen Billiar et al. "Effects of carbodiimide crosslinking conditions on the physical properties of laminated intestinal submucosa", J. Biomed. Mater. Res. 2001, 51(1): 101-108.

Toshimitsu Momose et al. "Surface modification of extrasynovial tendon by chemically modified hyaluronic acid coating" J. Biomed. Mater. Res. 2002, 59: 219-224.

Handbook of Biodegradable Polymers Hardwood Press 1997 (251-272).

Cohn et al., "Biodegradable PEO/PLA block copolymers," Journal of Biomedical Materials Research, 1988, 22 (993-1009).

"Polymer Preprints" (ACS Division of Polymer Chemistry), 1989. 30 (1): 498.

The Encyclopedia of Polymer Science, 1988 (13) 31-41.

"Handbook of Biodegradable Polymers" Hardwood Press 1977 (161-182).

"Handbook of Biodegradable Polymers" Hardwood Press 1997 (99-118).

DiSilvestro et al., "Effects of Cross-Linking on the Mechanical Properties of a Porous Foam Scaffold of Small Intestine Submucosa", Society for Biomaterials 29th Annual Meeting Transactions, 2003, pp. 88.

Allman et al., "The Th2-Restricted Immune Response to Xenogeneic Small Intestinal Submucosa Does Not Influence Systemic Protective Immunity to Viral and Bacterial Pathogens", Tissue Engineering, vol. 8, No. 1, 2002, pp. 53-62.

Ide et al., "Collagen Hybridization with Poly(I-Lactic Acid) Braid Promotes Ligament Cell Migration", Mater. Sci. Eng. C, 17(1-2), 95-99 (2001).

Bercovy et al., "Carbon-PGLA Prosthesis for Ligament Reconstruction Experimental Basis and Short Term Results in Man", Clin. Orthop. Relat. Res., (196), 159-68 (1985).

Zhu et al, "Immobilization of Biomacromolecules onto Aminolyzed Poly(L-lactic acid) toward Acceleration of Endothelium Regeneration", Tissue Engineering, v 10, pp. 53-61, 2004.

Cheng & Teoh, "Surface modification of ultra thin poly (ÿ caprolactone) films using acrylic acid and collagen", Biomaterials, v25(11), pp. 1991-2001, 2004.

Wan et al., "Cell adhesion on gaseous plasma modified poly-(L-lactide) surface under shear stress field", Biomaterials, v24(21), pp. 3757-3764, 2003.

Yang et al., "Effect of surface treatment on the biocompatibility of microbial polyhydroxyalkanoates", Biomaterials, v 23 (5), pp. 1391-1397, 2002.

Croll et al., "Controllable surface modification of Poly(lactic-co-glycolic acid) (PLGA) by hydrolysis or aminolysis I: physical, chemical, and theoretical aspects", Biomacromolecules, Mar.-Apr. 2004, 5(2): 463-473.

Kwon et al., "Fibroblast culture on surface-modified poly (glycolide-co-ÿ-caprolactone) scaffold for soft tissue regeneration", J. Biomater Sci Polym ed. 2001, 12(10) 1147-60.

Gastel JA, Muirhead WR, Lifrak JT, Fadale PD, Hulstyn MJ, Labrador DP "Meniscal tissue regeneration using a collagenous biomaterial derived from porcine small intestine submucosa", Arthroscopy, Feb.; 17(2): 151-159.

Tan W, Krishnaraj R, Desai TA "Evaluation of nanostructured composite collagen-chitosan matrices for tissue engineering", Tissue Eng Apr.; 7(2): 203-210, 2001.

Arnoczky SP "Building a meniscus", Biological considerations, Clin Orthop Oct.; 367 (suppl), S244-53, 1999.

Metcalf et al., "Surgical technique for xenograft (SIS) augmentation of rotator-cuff repairs", Op Tech Orthop, 12(3): 204-208, 2002.

Courtney et al., "Modification of polymer surfaces: optimization of approaches", Perfusion, v 18 (11), pp. 33-39, 2003.

Zhang et al., Design of nanostructured biological materials through self-assembly of peptides and proteins, MIT Current Opinion in chemical Biology, 2002, 6:865-871.

Hodde and Hiles, "Bioactive FGF-2 in sterilized extracellular matrix", Wounds, 13(5): 195-201 (2001).

O'Meara, Patrick, "The basic science of meniscus repair," Orthopaedic review, Jun. 1993, pp. 681-686.

Clearfix screw advertisement, 1998, Innovasive devices, Inc.

Winters and Justin, "Clearfix meniscal screw", Innovasive devices, Inc. 1998.

Surgical dynamics, meniscal stapler advertisement, 1997.

Bionix implants, Meniscus arrow advertisement, 1996.

Instrument makar, inc., Meniscus mender II, 1989.

William G. Clancy, Jr., M.D., and Ben K. Graf, M.D., "Arthroscopic Meniscal Repair," ACUFEX Microsurigal Inc., advertisement, 1988.

European Search Report for European Patent Application 02750033.9-1219, Mar. 16, 2007, 6 pgs.

* cited by examiner

CARTILAGE REPAIR AND REGENERATION DEVICE

This application claims priority to U.S. Provisional Application No. 60/388,724, filed Jun. 14, 2002, and U.S. Provisional Application No. 60/305,786, filed Jul. 16, 2001, hereby incorporated by reference.

CROSS REFERENCE

Cross reference is made to copending U.S. patent applications Ser. No. 10/195,795 entitled "Meniscus Regeneration Device and Method"; Ser. No. 10/195,719 entitled "Devices from Naturally Occurring Biologically Derived Materials"; Ser. No. 10/195,347 entitled "Cartilage Repair Apparatus and Method"; Ser. No. 10/195,344 entitled "Unitary Surgical Device and Method"; Ser. No. 10/195,341 entitled "Hybrid Biologic/Synthetic Porous Extracellular Matrix Scaffolds"; Ser. No. 10/195,354 entitled "Porous Extracellular Matrix Scaffold and Method"; Ser. No. 10/195,334 entitled "Cartilage Repair and Regeneration Scaffolds and Method"; and Ser. No. 10/195,633 entitled "Porous Delivery Scaffold and Method", each of which is assigned to the same assignee as the present application, each of which is filed concurrently herewith, and each of which is hereby incorporated by reference. Cross reference is also made to U.S. patent application Ser. No. 10/172,347 entitled "Hybrid Biologic-Synthetic Bioabsorbable Scaffolds" which was filed on Jun. 14, 2002, which is assigned to the same assignee as the present application, and which is hereby incorporated by reference.

BACKGROUND OF THE INVENTION

Articular cartilage is a type of hyaline cartilage that lines the surfaces of the opposing bones in a diarthrodial joint (e.g. knee, hip, shoulder, etc.). Articular cartilage provides a near-frictionless articulation between the bones, while also functioning to absorb and transmit the compressive and shear forces encountered in the joint. Further, since the tissue associated with articular cartilage is aneural, these load absorbing and transmitting functions occur in a painless fashion in a healthy joint.

Fibrocartilage is found in diarthrodial joints, symphyseal joints, intervertebral discs, articular discs, as inclusions in certain tendons that wrap around a pulley, and at insertion sites of ligaments and tendons into bone. Made of a mixture of collagen type I and type II fibers, fibrocartilage can also be damaged, causing pain in the affected joint. It is understood for purposes of this application that the term "cartilage" includes articular cartilage and fibrocartilage.

When cartilage tissue is no longer healthy it can cause debilitating pain in the joint. For example, articular cartilage health can be affected by disease, aging, or trauma, all of which primarily involve a breakdown of the matrix consisting of a dense network of proteoglycan aggregates, collagen fibers, and other smaller matrix proteins. Tissue cells are unable to induce an adequate healing response because they are unable to migrate, being enclosed in lacunae surrounded by a dense matrix. Further, since the tissue is avascular, initiation of healing by circulating cells is limited. Similarly, damage or degeneration of knee fibrocartilage i.e. the menisci, is a common occurrence. A damaged or degenerated meniscus has little ability to heal or repair itself because the pathology frequently occurs in the avascular part of the tissue.

Several articular cartilage repair strategies have been attempted in the past. These include surgical techniques such as microfracturing or performing abrasion arthroplasty on the bone bed to gain vascular access, and hence, stimulate extrinsic repair in the defective region. The long-term outcome of these techniques, however, has been known to result in mechanically inferior fibrocartilagenous tissue.

Another surgical technique is mosaicplasty or osteochondral autograft transfer system (OATS). In this case, cylindrical plugs of healthy articular cartilage from a low-load bearing region of the knee are taken and transplanted into the defective region. This technique, however, can result in excessive donor-site morbidity and associated pain. Additionally, surgeons have reported that the gaps between the round transplants are frequently filled with fibrocartilage which can eventually erode away, thus potentially compromising the integrity of repair throughout the affected area.

The only FDA-approved cartilage treatment product in the market involves autologous chondrocyte implantation (CartiCel™). Autologous chondrocyte implantation involves performing an initial biopsy of healthy cartilage from the patient, isolating the cells from the tissue, expanding the cells in vitro by passaging them in culture, and then reintroducing the cells into the defective area. The cells are retained within the defect by applying a periosteal tissue patch over the defect, suturing the edges of the patch to the host tissue, and then sealing with fibrin glue. The efficacy of this expensive procedure, however, has recently been put into question by studies that have shown that only a few of the injected cells are retained within the defect and that they may not significantly contribute to the repair process. The healing observed is similar to that observed with microfracture or abrasion of the bone bed, suggesting that it is the preparation of the bone bed and not the introduction of the cells that facilitates the healing process.

Tissue engineering strategies for healing cartilage are being investigated by several academic and commercial teams and show some promise. One approach primarily involves using a carrier or a scaffold to deliver cells or stimulants to the defect site. The scaffold material can be a purified biologic polymer in the form of a porous scaffold or a gel (purified collagens, glycoproteins, proteoglycans, polysaccharides, or the like in various combinations) or porous scaffolds of synthetic biodegradable polymers (PLA, PGA, PDO, PCL, or the like, in various combinations). Several challenges remain with this approach, however. Some of these challenges include retention of the active stimulant at the defect site, inability to control the rate of release of the stimulant (resulting in tissue necrosis due to overdose), and cytotoxicity of the cells due to the degradation by-products of the synthetic polymers.

In another technique, various collagen scaffolds have been used to provide a scaffold for repair and regeneration of damaged cartilage tissue. U.S. Pat. No. 6,042,610 to ReGen Biologics, hereby incorporated by reference, discloses the use of a device to regenerate meniscal fibrocartilage. The disclosed device comprises a bioabsorbable material made at least in part from purified collagen and glycosaminoglycans (GAG). Purified collagen and glycosaminoglycans are colyophilized to create a foam and then cross-linked to form the device. The device can be used to provide augmentation for a damaged meniscus. Related U.S. Pat. Nos. 5,735,903, 5,479, 033, 5,306,311, 5,007,934, and 4,880,429 also disclose a meniscal augmentation device for establishing a scaffold adapted for ingrowth of meniscal fibrochondrocyts.

It is also known to use naturally occurring extracellular matrices (ECMs) to provide a scaffold for tissue repair and regeneration. One such ECM is small intestine submucosa (SIS). SIS has been described as a natural biomaterial used to repair, support, and stabilize a wide variety of anatomical defects and traumatic injuries. See, for example, Cook®

Online New Release provided by Cook Biotech at "www-.cookgroup.com". The SIS material is reported to be a naturally-occurring collageneous matrix derived from porcine small intestinal submucosa that models the qualities of its host when implanted in human soft tissues. Further, it is taught that the SIS material provides a natural matrix with a three-dimensional structure and biochemical composition that attracts host cells and supports tissue remodeling. SIS products, such as Oasis material and Surgisis material, are commercially available from Cook Biotech, Bloomington, Ind.

An SIS product referred to as RESTORE Orthobiologic Implant is available from DePuy Orthopaedics, Inc. in Warsaw, Indiana. The DePuy product is described for use during rotator cuff surgery, and is provided as a resorbable framework that allows the rotator cuff tendon to regenerate itself. The RESTORE Implant is derived from porcine small intestine submucosa that has been cleaned, disinfected, and sterilized. Small intestine submucosa (SIS) has been described as a naturally-occurring ECM composed primarily of collagenous proteins. Other biological molecules, such as growth factors, glycosaminoglycans, etc., have also been identified in SIS. See Hodde et al., Tissue Eng. 2(3): 209-217 (1996); Voytik-Harbin et al., J. Cell Biochem., 67:478-491 (1997); McPherson and Badylak, Tissue Eng., 4(1): 75-83 (1998); Hodde et al., Endothelium, 8(1):11-24 (2001); Hodde and Hiles, Wounds, 13(5): 195-201 (2001); Hurst and Bonner, J. Biomater. Sci. Polym. Ed., 12(11) 1267-1279 (2001); Hodde et al., Biomaterial, 23(8): 1841-1848 (2002); and Hodde, Tissue Eng., 8(2): 295-308 (2002), all of which are incorporated by reference herein. During seven years of preclinical testing in animals, there were no incidences of infection transmission from the implant to the host, and the SIS material has not decreased the systemic activity of the immune system. See Allman et al., Transplant, 17(11): 1631-1640 (2001); Allman et al., Tissue Eng., 8(1): 53-62 (2002).

While small intestine submucosa is available, other sources of submucosa are known to be effective for tissue remodeling. These sources include, but are not limited to, stomach, bladder, alimentary, respiratory, or genital submucosa, or liver basement membrane. See, e.g., U.S. Pat. Nos. 6,171,344, 6,099,567, and 5,554,389, hereby incorporated by reference. Further, while SIS is most often porcine derived, it is known that these various submucosa materials may be derived from non-porcine sources, including bovine and ovine sources. Additionally, other collageneous matrices are known, for example lamina propria and stratum compactum.

For the purposes of this invention, it is within the definition of a naturally occurring ECM to clean, delaminate, and/or comminute the ECM, or even to cross-link the collagen fibers within the ECM. It is also within the definition of naturally occurring ECM to fully or partially remove one or more sub-components of the naturally occurring ECM. However, it is not within the definition of a naturally occurring ECM to extract and purify the natural collagen or other components or sub-components of the ECM and reform a matrix material from the purified natural collagen or other components or sub-components of the ECM. Thus, while reference is made to SIS, it is understood that other naturally occurring ECMs are within the scope of this invention. Thus, in this application, the terms "naturally occurring extracellular matrix" or "naturally occurring ECM" are intended to refer to extracellular matrix material that has been cleaned, disinfected, sterilized, and optionally cross-linked. The terms "naturally occurring ECM" and "naturally occurring extracellular matrix" are also intended to include foam material made from naturally occurring ECM as described in U.S. patent application Ser. No. 10/195,354 entitled "Porous Extracellular Matrix Scaffold and Method", the toughened material made from naturally occurring ECM as described in U.S. patent application Ser. No. 10/195,795 entitled "Meniscus Regeneration Device and Method", and the hardened material made from naturally occurring ECM as described in U.S. patent application Ser. No. 10/195,719 entitled "Devices from Naturally Occurring Biologically Derived Materials", all filed concurrently herewith and incorporated by reference.

The following patents, hereby incorporated by reference, disclose the use of ECMs for the regeneration and repair of various tissues: U.S. Pat. Nos. 6,379,710; 6,334,872; 6,187,039; 6,176,880; 6,126,686; 6,099,567; 6,096,347; 5,997,575; 5,993,844; 5,968,096; 5,955,110; 5,922,028; 5,885,619; 5,788,625; 5,733,337; 5,762,966; 5,755,791; 5,753,267; 5,711,969; 5,645,860; 5,641,518; 5,554,389; 5,516,533; 5,460,962; 5,445,833; 5,372,821; 5,352,463; 5,281,422; and 5,275,826.

It is also known to promote cartilage growth using glycosaminoglycans (GAG), such as hyaluronic acid (HA), dermatan sulfate, heparan sulfate, chondroitin sulfates, keratin sulfate, etc. See, e.g., U.S. Pat. Nos. 6,251,876 and 6,288,043, hereby incorporated by reference. GAGs are naturally found mostly in the extracellular matrix and on the cell surface as proteoglycans. These macromolecules are secreted by cells and play a role in both signal transduction and storage of some growth factors. In addition to the biological functions, the viscoelastic properties of GAGs provide a mechanical function by providing lubrication within a joint, to decrease friction. Hyaluronic acid is a natural component of the extracellular matrix of most cartilage tissues. HA is a linear polymer made up of repeating GAG disaccharide units of Dglucuronic acid and N-acetylglycosamine in $\beta(1-3)$ and $\beta(1-4)$ linkages. Illustratively HA can have a molecular weight ranging from about 300,000 kDa to about 6,000,000 kDa and can be uncrosslinked, naturally crosslinked, or crosslinked using mechanical, chemical, or enzymatic methods. The effect of treating extrasynovial tendons with HA and chemically modified HA has also been studied with reference to tendon gliding resistance and tendon adhesions to surrounding tissue after repair. Momose, Amadio, Sun, Chunfeng Zhao, Zobitz, Harrington and An, "Surface Modification of Extrasynovial Tendon by Chemically Modified Hyaluronic Acid Coating," J. Biomed. Mater. Res. 59: 219-224 (2002).

SUMMARY OF THE INVENTION

It has been found that the combination of SIS and HA produces a synergistic effect in cartilage repair. Healing rates and/or quantity of healing is better than the healing expected from additive effects of SIS and HA alone. Additionally, it has been found that retention of the HA at the defect site is not problematic when used with an ECM scaffold, and co-administration of the ECM and HA does not require the HA to be crosslinked to the ECM material. Thus, the present invention provides methods for the repair of damaged or diseased cartilagenous tissue, wherein an ECM material and HA are co-administered to the cartilagenous tissue defect.

In addition to HA, GAGs such as dermatan sulfate, heparan sulfate, chondroitin sulfate and keratan sulfate are also expected to be usable with the present invention. As used herein, "biological lubricant" is used to identify the aforementioned materials and others such as synovial fluid and components thereof, including mucinous glycoproteins (for example lubricin), tribonectins, articular cartilage superficial zone proteins, surface-active phospholipids, and lubricating glycoproteins I, II; vitronectin; and rooster comb hyaluronate (e.g. commercially available HEALON®, (Pharmacia Corporation, Peapack, New Jersey), for example, and mixtures thereof. Such materials serve both biological and mechanical functions: they play a biological role in directly and indirectly influencing cellular behavior by being involved in signal transduction alone or in conjunction with other extracellular matrix components such as growth factors, glycoproteins, collagens etc., and a mechanical role in providing lubrication. The use of the expression "biological lubricant" is intended to encompass materials that provide some biological function (influencing cellular behavior), some mechanical function (lubrication), both of these functions, and mixtures of such materials.

It is believed that some commercially-available biological lubricants can be used in the practice of the present invention. Examples of such commercially-available lubricants include: ARTHREASE™ high molecular weight sodium hyaluronate, available in Europe from DePuy Orthopaedics, Inc. of Warsaw, Ind.; SYNVISC® Hylan G-F 20, manufactured by Biomatrix, Inc., of Ridgefield, N.J. and distributed by Wyeth-Ayerst Pharmaceuticals of Philadelphia, Pa.; and HYLAGAN® sodium hyaluronate, available from Sanofi-Synthelabo, Inc., of New York, N.Y. The expressions "HA", "GAG" and "biological lubricant" are intended to encompass these materials unless otherwise expressly excluded. It should be understood that there may be other salts of hyaluronic acid that may be used in the present invention, and the expressions "HA", "GAG" and "biological lubricant" should be understood to encompass such salts unless expressly excluded.

In one embodiment of the present invention, a method is provided wherein a scaffold, for example made from an ECM material, is implanted into the defect. The defect may be in a meniscus or other articular cartilage. The biological lubricant, which can be a GAG or HA for example, is administered separately, either at the time of surgery or via injection subsequent to closure of the incision. Optionally, a series of additional injections may be administered over a period of time. In either case, the injection may be made intra-articularly.

In another embodiment, a method is provided wherein a scaffold, for example an ECM material, and the biological lubricant are administered to the defect together. The ECM material may be saturated with the biological lubricant at the time of surgery. Alternatively, the ECM material may be saturated with the biological lubricant at the time of manufacture, and may be packaged together. Optionally, a series of additional injections may be administered in this method as well.

Other methods are provided for administering ECM implant and a biological lubricant. The biological lubricant can be physically or chemically crosslinked to the ECM implant at the time of manufacture. Illustratively, the biological lubricant can be dried on the ECM implant at manufacture. The biological lubricant and the ECM material can be co-lyophilized. The biological lubricant can be covalently bonded to the ECM material. Finally, combinations of the above methods may be used; for example, an implant of covalently bonded ECM and biological lubricant can be implanted and additional intra-articular injections of the same or different biological lubricants can be made at surgery, post-operatively, or both at surgery and postoperatively.

In still another embodiment, an implantable device is provided comprising an ECM material saturated with a biological lubricant.

DETAILED DESCRIPTION

Figure 1:
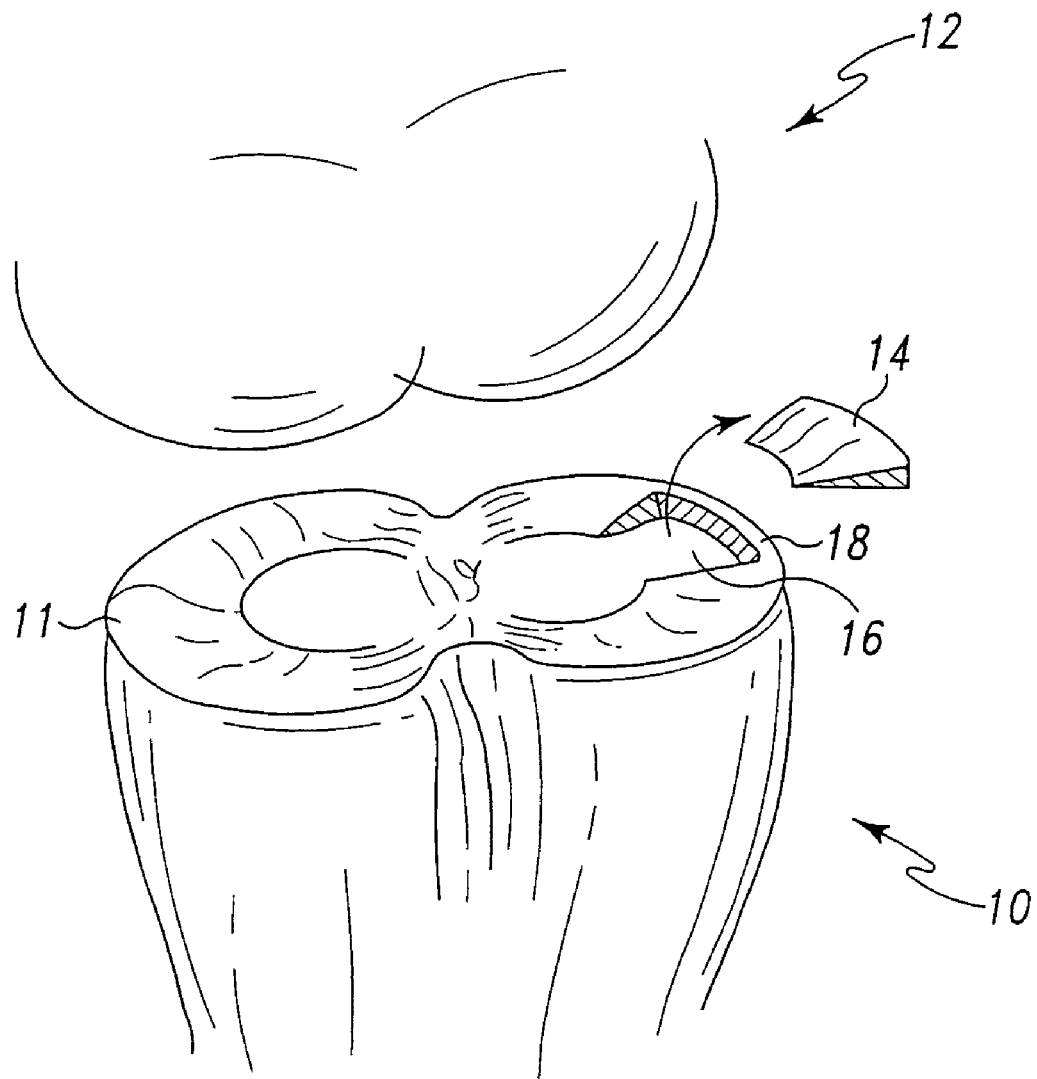
FIG. 1 is a diagrammatical view showing a tibial platform with a typical meniscus structure on the platform and a portion of the meniscus removed for illustration purposes, the tibia platform being below the condyles of the femur.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Referring to FIG. 1, it will be seen that a tibial platform 10 below the condyles 12 of a knee support a meniscus 11 from which an illustrative defective portion 14 is removed to leave a wedge-shaped space 16. In the removal process, the surgeon will often leave an outer rim 18 of the meniscus. The meniscus provides a large surface of articulation between the otherwise incongruent surfaces of the tibia platform or plateau and the femur condyles (such indicated at 12). The meniscus serves to reduce contact stresses and wear in the knee joint.

The portion 14 removed from the structure shown in FIG. 1 includes a portion of the original meniscus which was within the avascular zone, particularly the radially inner portion, and may include a portion of the original meniscus which was within the vascular zone.

Figure 2:
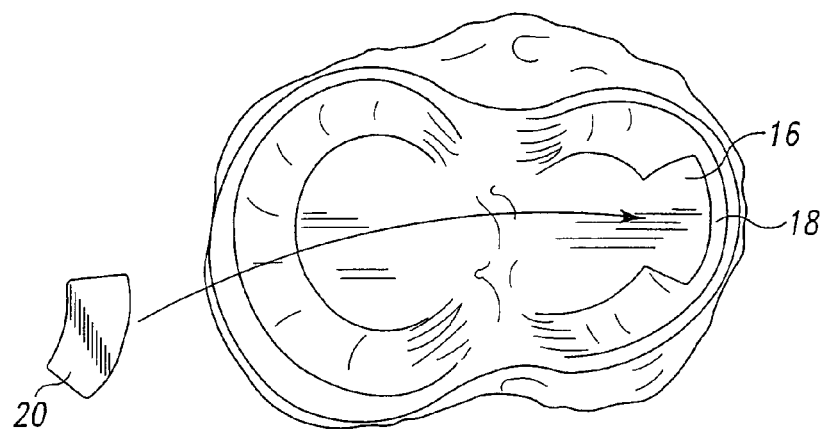
FIG. 2 is a view looking down at the tibial platform and showing diagrammatically the insertion of an illustrative meniscal repair device to replace the portion of the meniscus removed.
Figure 3:
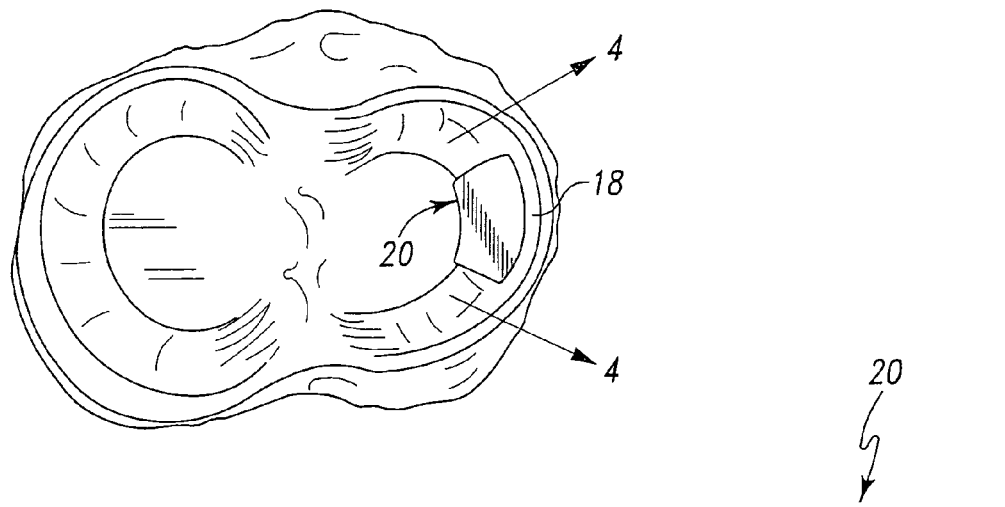
FIG. 3 shows the inserted device in a position to be attached to the portions of the meniscus remaining after the injured portion is removed.
Figure 4:
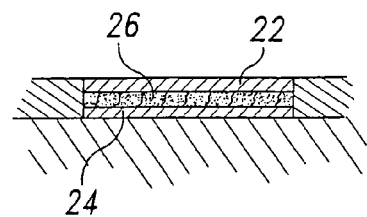
FIG. 4 is a sectional view taken from FIG. 3 along the lines 4-4.

FIG. 2 shows how an ECM device may illustratively be inserted into the space 16 to be against the outer rim 18. This illustrative device 20 is shown in FIGS. 3 and 4 in position filling the space 16 and against the rim 18 left by the surgeon. FIG. 4 shows the device as comprising an upper cover or upper panel 22 and a lower cover or lower panel 24. These panels 22, 24, which may illustratively be angularly related, will define an internal space 26 between the covers. Internal space 26 may be filled with a biological material or a biological structure providing a framework for regeneration of the meniscus into the space 16.

Device 20 may be inserted, for example, in arthroscopic surgery through portals provided in the outer anterior surface of the knee opening into the knee cavity between the condyles 12 and the tibial platform 10. However, any surgical procedure to insert a device into damaged cartilage is within the scope of the present invention. As shown, the upper cover 22 of the device 20 will serve as a bearing surface for the condyle 12 disposed thereabove and be subjected to the compression and stress forces involved in articulation of the knee. The condyle will move upon the upper surface of the cover 22. The device 20 will serve as a cushion or pillow for handling the compression load provided by the knee.

Figure 5:
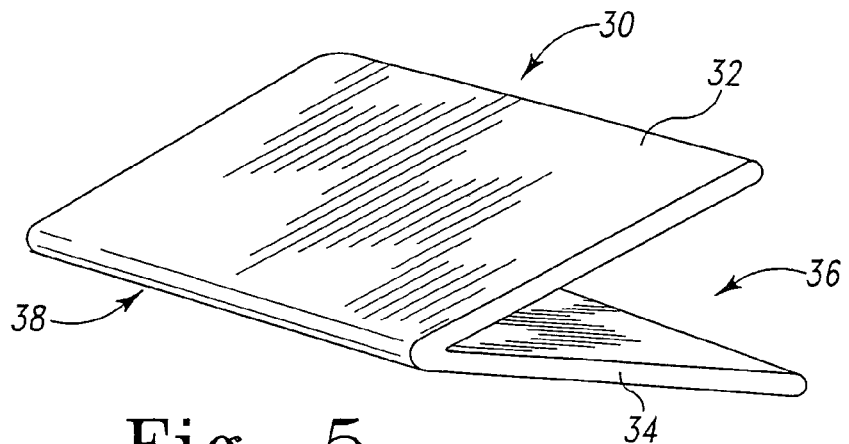
FIG. 5 is a perspective view showing an open wedge-shaped device comprising an upper panel and a lower panel angularly separated to define an apex portion and a base portion.
Figure 6:
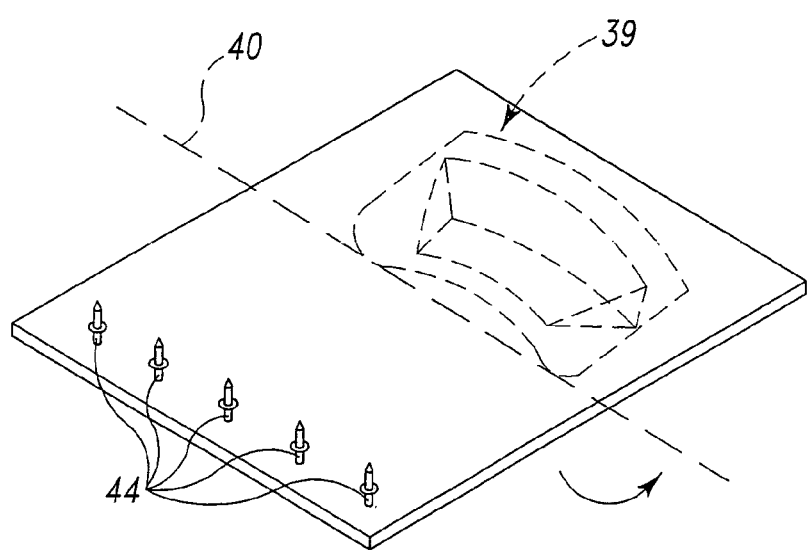
FIG. 6 shows a wedge shaped device prior to folding with a pocket shown in imaginary lines formed in the device.
Figure 7:
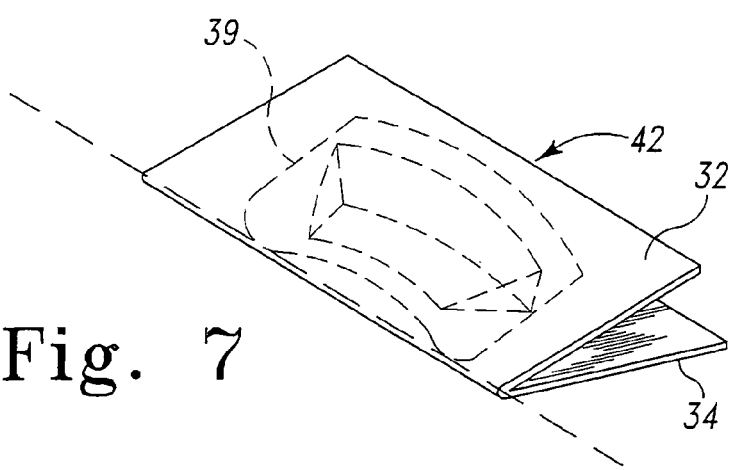
FIG. 7 shows a further step in the process in making the device shown in FIG. 6 to produce a filled, wedge-shaped device.

Turning to FIGS. 5, 6 and 7, it will be seen that an illustrative device is somewhat diagrammatically illustrated. The illustrative device 30 includes an upper panel 32 and a lower panel 34 defining a wedge-shaped device having a base portion 36 and an apex portion 38. FIG. 6 suggests that the device may include a formed wedge-shaped cavity 39 (illustrated in phantom) and that the device may be folded about a fold line 40 to provide a device such as indicated at 42 in FIG. 7. While the FIG. 5 device 30 suggests an open wedge-shaped design, the device 42 in FIG. 7 suggests that, between the upper and lower panels 32, 34 a mass of biological material may be disposed. In FIG. 6, a plurality of tacks 44 are shown attached to one of the two panels of the device to be used for securing the device to surrounding tissue in the knee. The panels 32, 34 may be trimmed to the desired wedge shape.

Panels 32, 34 are made from an ECM, illustratively SIS. In one embodiment, a plurality of layers of a naturally occurring ECM such as SIS may be layered together to form panels 32, 34. Optionally, the panels may be toughened, to better withstand the forces within the joint. Copending U.S. application Ser. No. 10/195,795 entitled "Meniscus Regeneration Device and Method", already incorporated by reference, teaches methods for toughening the panels. The mass of biological material may comprise, for example, comminuted ECM, fibrin, platelet rich plasma (PRP), blood clot, or some combination thereof.

Figure 8:
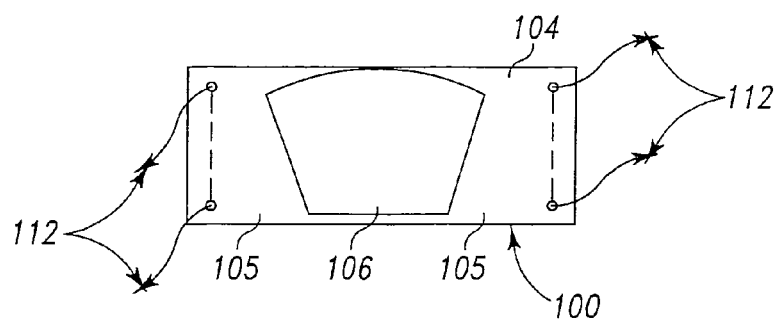
FIG. 8 is a top view of a ECM device used for the repair of a meniscal defect and having barbs for attachment.
Figure 9:
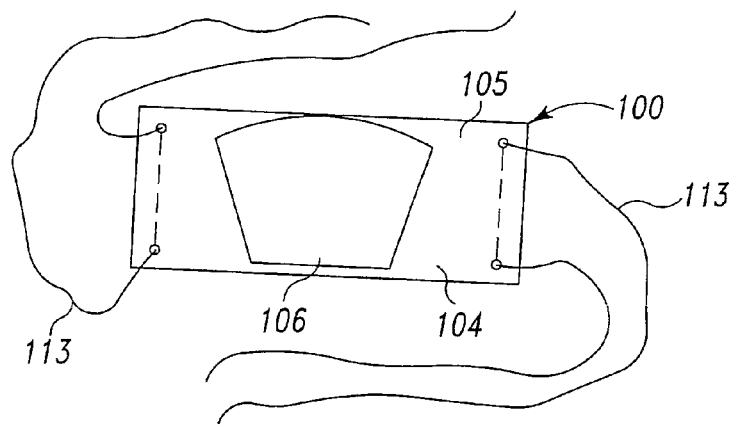
FIG. 9 is a top view of a device similar to that shown in FIG. 1, except having sutures for attachment.
Figure 10:
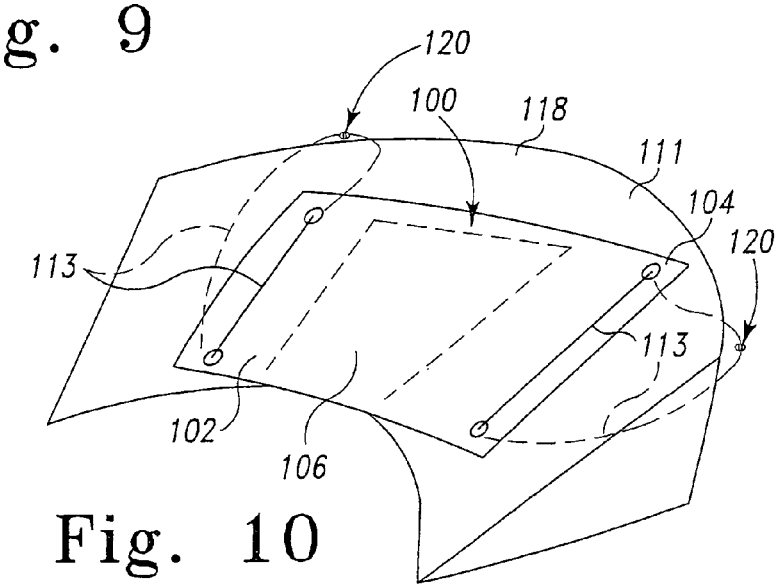
FIG. 10 is a perspective, partially cut-away view of a meniscus with the device of FIG. 1 inserted into the meniscus.

Referring now to FIGS. 8-10, there are shown devices similar to those shown in FIGS. 6-7, except that device 100 need not be wedge shaped. Device 100 comprises panels 102 and 104, with a pillow 106 of biological material shaped to fill the void in meniscus 111 left after a partial meniscectomy, as illustrated in FIG. 1. The pillow is placed between panels 102 and 104. In the illustrative embodiment, pillow 106 is smaller than panels 102 and 104, and wing portions 105 of panels 102 and 104 extend beyond pillow 106.

As shown in FIG. 8, device 100 may be provided with barbed darts 112 extending from wings 105. A needle or similar device would be used to push the barbed darts 112 into or through the meniscus to secure device 100 to the meniscus. Barbed darts may be made of any biocompatable material sufficiently rigid to secure device 100 to the meniscus. Barbed darts 112 may be provided integrally with device 100 or may be added by the surgeon prior to insertion of the device.

The device 100 illustrated in FIG. 9 is similar to the device shown in FIG. 8, except that instead of barbed darts, the device of FIG. 9 is provided with sutures 113. The device of FIG. 9 may be affixed to the meniscus in a manner similar to that of the device of FIG. 8. A needle or similar device would be used to push the sutures 113 through the meniscus. As illustrated in FIG. 10, the sutures may be tied together on the outside of the meniscus to form knots 120 that secure device 100 in place.

While in the various embodiments discussed herein, tacks and sutures have been shown for anchoring the devices, it will be appreciated that the devices may be anchored by any other method at the choice of the surgeon.

Figure 11:
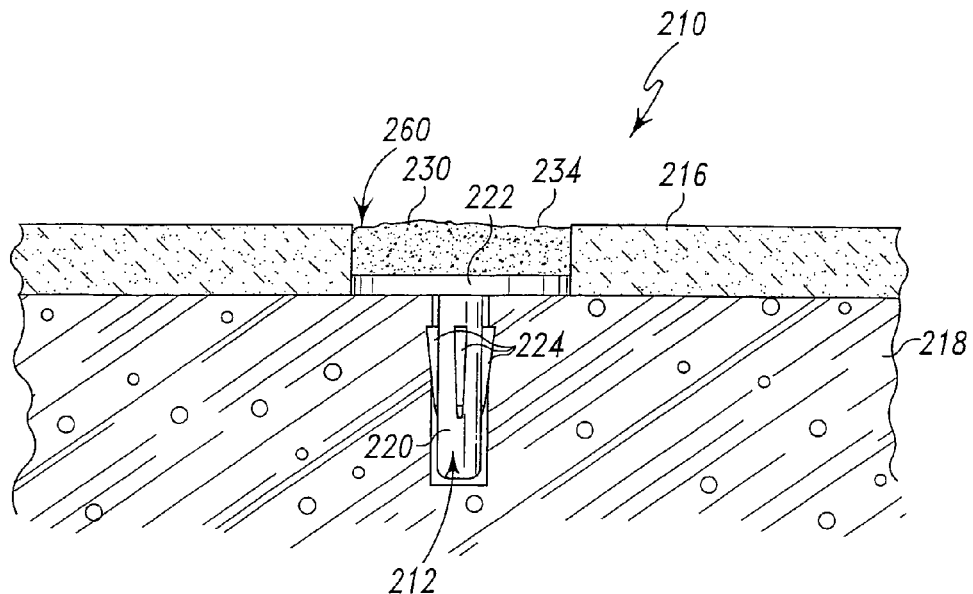
FIG. 11 is a cross sectional view of a cartilage repair device implanted in subchondral bone, note that the anchor is shown in elevation rather than cross section for clarity of description.
Figure 12:
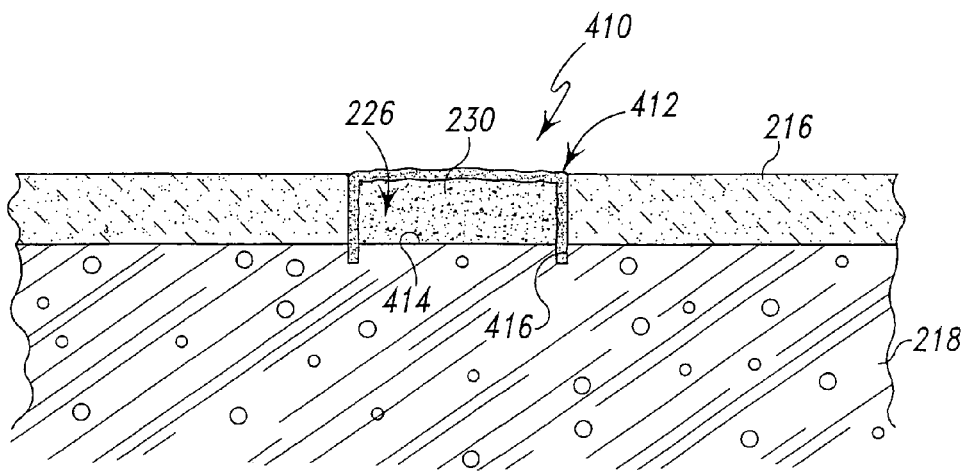
FIG. 12 is a cross sectional view of a cartilage repair device which uses an alternative embodiment of an anchor.

FIGS. 11 and 12 illustrate several scaffolds that can be used in conjunction with a biological lubricant for cartilage repair. Referring now to FIG. 11, a cartilage repair device 210 is provided for repairing damaged or diseased cartilage. The device 210 includes an anchor 212 which is anchored or otherwise positioned in an opening formed in both a section of native cartilage 216 and the underlying subchondral bone 218. The anchor 212 is configured to be secured in an area from which damaged, diseased, or destroyed native cartilage and possibly bone have been removed. The anchor 212 includes an elongated central body portion 220 and a head portion 222. The body portion 220 extends downwardly from a lower surface of the head portion 222. As shown in FIG. 11, the body portion 220 may have a number of barbs 224 extending therefrom for engaging the sidewalls of the opening formed in the bone 218. In the illustrative embodiment described herein, the barbs 224 extend radially outwardly and are inclined slightly toward the head portion 222 of the anchor 212.

The cartilage repair device 210 also includes a plug 226. The plug 226 is secured to the anchor 212. Specifically, the plug 226 is secured to the upper surface of the head portion 222 of the anchor 212. The plug 226 allows for communication across the removed portion (i.e., the portion of the native cartilage 216 from which the damaged or diseased cartilage has been removed) and the adjacent healthy cartilage. As such, the plug 226 functions as a chondrogenic growth-supporting matrix for promoting a positive cellular response in an effort to achieve articular cartilage regeneration.

The anchor 212 of the cartilage repair device 210 may be constructed of numerous types of synthetic or naturally occurring materials. For example, the anchor 212 may be constructed with a bioabsorbable polymer. Examples of such polymers include: polyesters of [alpha]-hydroxycarboxylic acids, such as poly(L-lactide) (PLLA), polyglycolide (PGA); poly-p-dioxanone (PDO); polycaprolactone (PCL); and any other bioresorbable and biocompatible polymer, co-polymer or mixture of polymers or co-polymers that are commonly used in the construction of prosthetic implants. Moreover, the anchor 212 may be constructed with a naturally occurring material such as a naturally occurring ECM (e.g., SIS). In such a case, the head portion 222 and body portion 220 of the anchor 212 may be configured as monolithic structures formed from naturally occurring ECM which is cured to be rigid and hardened to facilitate attachment to the bone 218. As such, it should be appreciated that the ECM material from which the anchor 212 is fabricated is cured to produce a structure which possesses the necessary hardness and toughness to allow the anchor 212 to be driven into bone tissue (i.e., the subchondral bone 218). See U.S. patent application Ser. No. 10/195,719 entitled "Devices from Naturally Occurring Biologically Derived Materials", already incorporated by reference. It should be understood that the material selected for the anchor 212 may also comprise mixtures or composites of materials. For example, the anchor 212 could comprise both a polymer and ECM material.

As mentioned above, the plug 226, which is fixed to the anchor 212, functions as a chondrogenic growth-supporting matrix for promoting vascular invasion and cellular proliferation in an effort to achieve articular cartilage regeneration. A central body 230 of the plug 226 is configured as a porous structure constructed from a naturally occurring ECM material such as SIS. When anchored to a defective area of cartilage, cells can migrate into and proliferate within the plug 226, biodegrade the plug 226 while, at the same time, synthesize new and healthy tissue to heal the defective area. The plug 226 may be made out of comminuted and/or lyophilized naturally occurring ECM (e.g. SIS) with the desired porosity and material density. Specifically, the material density and/or porosity of the plug 226 may be varied to control cell migration and proliferation. The cells can migrate from adjacent tissue or from synovial fluid. The ECM from which the plug 226 is constructed also may be formed to have a structural rigidity sufficient to withstand the compression and shear stress to which the cartilage 216 is subjected. As such, the ECM from which the plug 226 is constructed to have the structural rigidity necessary to bear the forces associated with the other bone.

One particularly useful material for fabricating the plug 226 is a porous scaffold or "foam" composed of naturally occurring ECM. For example, the plug 226 may be constructed from a porous SIS foam. In such a manner, both the material density and the pore size of the foam plug 226 may be varied to fit the needs of a given plug design. Such foams may be fabricated by lyophilizing (i.e., freeze-drying) comminuted ECM (i.e., SIS) suspended in water. The material density and pore size of the resultant foam may be varied by controlling, among other things, the rate of freezing of the comminuted SIS suspension and/or the amount of water or moisture content in the comminuted SIS at the on-set of the freezing process. See U.S. patent application Ser. No. 10/195,347 entitled "Cartilage Repair Apparatus and Method" and Ser. No. 10/195,354 entitled "Porous Extracellular Matrix Scaffold and Method", already incorporated by reference.

Referring now to FIG. 12, there is shown another embodiment of a cartilage repair device (hereinafter referred to with reference numeral 410). The cartilage repair device 410 is somewhat similar to the cartilage repair device 210. As such, the same reference numerals are used in FIG. 12 to identify components which have previously been discussed, with additional discussion thereof being unwarranted. The cartilage repair device 410 includes an anchor 412 which is used in lieu of the anchor 212 described in regard to FIG. 11. In particular, in the embodiment shown in FIG. 12, the plug 226 is positioned in an osteochondral defect 414 without the use of a bottom-mounted anchor (i.e., the anchor 212 of FIG. 11). Similarly to as described above, the plug 226 is constructed out of comminuted and lyophilized naturally occurring ECM (e.g., SIS) having a desired porosity and material density.

The plug 226 is retained in the hole formed in the cartilage 216 and protected from in vivo forces by an annular shaped anchor 412. The anchor 412 may be provided in many different configurations which allow it to be press fit or otherwise anchored into the subchondral bone 218. For example, as shown in FIG. 12, the anchor 412 may be "bottle cap"-shaped so as to allow the anchor 412 to be press fit or otherwise secured into an annular groove 416 formed in the subchondral bone 218. The groove may be formed and the anchor may be shaped as described and shown in Patent Cooperation Treaty publication WO 01/39694 A2, published Jun. 7, 2001 entitled "Fixation Technology," the complete disclosure of which is incorporated by reference herein. Alternatively, the anchor 412 may be mechanically secured to the subchondral bone 218 by use of adhesive or other types of anchoring structures (e.g., barbs).

The anchor 412 of the cartilage repair device 410 may be constructed from numerous types of synthetic or naturally occurring materials. For example, the anchor 212 may be constructed with a bioabsorbable polymer such as PLLA, PGA, PDO, PCL, or any other such bioabsorbable polymer which is commonly used in the construction of prosthetic implants. Moreover, the anchor 412 may be constructed from a naturally occurring material such as a naturally occurring ECM (e.g., SIS) that is cured or otherwise fabricated to be rigid and hardened to facilitate attachment to the bone in the same manner as described above in regard to the anchor 212 and/or the plug 226 of FIG. 11.

In embodiments when the anchor 412 is constructed from ECM, one or more laminated or non-laminated sheets of the same or different ECM may be utilized. The sheets may surround the plug 226 on three sides, as shown in FIG. 12, or perhaps all four sides. Alternatively, the anchor may be constructed from formed (e.g., dried and machined) comminuted ECM material. In either configuration, the ECM material may be perforated and may be cured in a similar manner to as described above in regard to the anchor 212 or the plug 226.

The ECM device illustratively may be provided fresh, frozen, or lyophilized. In one embodiment, the device is saturated with HA prior to packaging. The HA may be crosslinked to the ECM device, illustratively mechanically, chemically, or enzymatically. In one embodiment, the HA is crosslinked to the articulation surface of the device (for example panel 102 of the device illustrated in FIG. 10 or plug 226 of FIG. 11).

Copending U.S. patent application Nos. 10/195,795 and 10/195,347 entitled "Meniscus Regeneration Device and Method" and "Cartilage Repair Apparatus and Method", filed concurrently and hereby incorporated by reference, disclose various additional devices for repairing damaged or diseased cartilage. Each of the devices is made in whole or part from an ECM material, illustratively SIS. In some embodiments, the SIS material is provided fresh, frozen, or lyophilized. Illustratively, as disclosed in these copending applications, depending upon the application, the SIS material may be laminated, foamed, comminuted, hardened, and/or toughened. Any of the devices disclosed in U.S. patent application Nos. 10/195,795 and 10/195,347, are suitable for use with the present invention. Devices with other configurations are also within the scope of this invention. Other forms of SIS may also be used within the scope of this invention. For example, the SIS may be powdered and optionally formed into a gel, as disclosed in U.S. Pat. No. 5,352,463. It is believed that the ECM devices provide a tissue growth-supporting matrix for promoting vascular invasion and cellular migration.

It is expected that the teachings of the present invention may also be advantageously combined with the teachings of the following U.S. Patent Applications filed concurrently herewith and which are incorporated by reference herein: 10/195,719 entitled "Devices from Naturally Occurring Biologically Derived Materials"; 10/195,344 entitled "Unitary Surgical Device and Method"; 10/195,341 entitled "Hybrid Biologic/Synthetic Porous Extracellular Matrix Scaffolds"; 10/195,354 entitled "Porous Extracellular Matrix Scaffold and Method"; and U.S. patent application Ser. No. 10/172,347 entitled "Hybrid Biologic-Synthetic Bioabsorbable Scaffolds." It is expected that the materials disclosed in those patent applications can be used in the present invention.

Similarly, it is expected that other materials may be combined with the biological lubricant or with the extracellular matrix. For example, bioactive agents, biologically-derived agents, cells, biocompatible polymers, biocompatible inorganic material and/or combinations thereof may be mixed with the biological lubricant.

"Bioactive agents" include one or more of the following: chemotactic agents; therapeutic agents (e.g. antibiotics, steroidal and non-steroidal analgesics and anti-inflammatories, anti-rejection agents such as immunosuppressants and anti-cancer drugs); various proteins (e.g. short chain peptides, bone morphogenic proteins, glycoprotein and lipoprotein); cell attachment mediators; biologically active ligands; integrin binding sequence; ligands; various growth and/or differentiation agents (e.g. epidermal growth factor, IGF-I, IGF-II, TGF-β, I-III, growth and differentiation factors, vascular endothelial growth factors, fibroblast growth factors, platelet derived growth factors, insulin derived growth factor and transforming growth factors, parathyroid hormone, parathyroid hormone related peptide, bFGF; TGF$_β$ superfamily factors; BMP-2; BMP-4; BMP-6; BMP-12; sonic hedgehog; GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments; and DNA plasmids. If other such substances have therapeutic value in the orthopaedic field, it is anticipated that at least some of these substances will have use in the present invention, and such substances should be included in the meaning of "bioactive agent" and "bioactive agents" unless expressly limited otherwise.

"Biologically derived agents" include one or more of the following: bone (autograft, allograft, and xenograft) and derivates of bone; cartilage (autograft, allograft, and xenograft), including, for example, meniscal tissue, and derivatives; ligament (autograft, allograft, and xenograft) and derivatives; derivatives of intestinal tissue (autograft, allograft, and xenograft), including for example submucosa; derivatives of stomach tissue (autograft, allograft, and xenograft), including for example submucosa; derivatives of bladder tissue (autograft, allograft, and xenograft), including for example submucosa; derivatives of alimentary tissue (autograft, allograft, and xenograft), including for example submucosa; derivatives of respiratory tissue (autograft, allograft, and xenograft), including for example submucosa; derivatives of genital tissue (autograft, allograft, and xenograft), including for example submucosa; derivatives of liver tissue (autograft, allograft, and xenograft), including for example liver basement membrane; derivatives of skin tissue; platelet rich plasma (PRP), platelet poor plasma, bone marrow aspirate, demineralized bone matrix, insulin derived growth factor, whole blood, fibrin and blood clot. Purified ECM and other collagen sources are also intended to be included within "biologically derived agents." If other such substances have therapeutic value in the orthopaedic field, it is anticipated that at least some of these substances will have use in the present invention, and such substances should be included in the meaning of "biologically-derived agent" and "biologically-derived agents" unless expressly limited otherwise.

"Biologically derived agents" also include bioremodelable collageneous tissue matrices. The expressions "bioremodelable collagenous tissue matrix" and "naturally occurring bioremodelable collageneous tissue matrix" include matrices derived from native tissue selected from the group consisting of skin, artery, vein, pericardium, heart valve, dura mater, ligament, bone, cartilage, bladder, liver, stomach, fascia and intestine, tendon, whatever the source. Although "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers. The term "bioremodelable collageneous tissue matrices" includes "extracellular matrices" within its definition.

It is understood and intended that there is substantial overlap between "bioremodelable collageneous tissue matrices" and "extracellular matrices"; the different expressions are used in this specification and claims to ensure complete coverage of the invention. It is believed that the teachings of the present invention will be useful for materials falling with both definitions.

"Cells" include one or more of the following: chondrocytes; fibrochondrocytes; osteocytes; osteoblasts; osteoclasts; synoviocytes; bone marrow cells; mesenchymal cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited otherwise. Illustratively, in one example of embodiments that are to be seeded with living cells such as chondrocytes, a sterilized implant may be subsequently seeded with living cells and packaged in an appropriate medium for the cell type used. For example, a cell culture medium comprising Dulbecco's Modified Eagles Medium (DMEM) can be used with standard additives such as non-essential amino acids, glucose, ascorbic acid, sodium pyrovate, fungicides, antibiotics, etc., in concentrations deemed appropriate for cell type, shipping conditions, etc.

"Biocompatible polymers" is intended to include both synthetic polymers and biopolymers (e.g. collagen). Examples of biocompatible polymers include: polyesters of [alpha]-hydroxycarboxylic acids, such as poly(L-lactide) (PLLA) and polyglycolide (PGA); poly-p-dioxanone (PDO); polycaprolactone (PCL); polyvinyl alchohol (PVA); polyethylene oxide (PEO); polymers disclosed in U.S Pat. Nos. 6,333,029 and 6,355,699; and any other bioresorbable and biocompatible polymer, co-polymer or mixture of polymers or co-polymers that are utilized in the construction of prosthetic implants. In addition, as new biocompatible, bioresorbable materials are developed, it is expected that at least some of them will be useful materials from which orthopaedic devices may be made. It should be understood that the above materials are identified by way of example only, and the present invention is not limited to any particular material unless expressly called for in the claims.

"Biocompatible inorganic materials" include materials such as hydroxyapatite, all calcium phosphates, alpha-tricalcium phosphate, beta-tricalcium phosphate, calcium carbonate, barium carbonate, calcium sulfate, barium sulfate, polymorphs of calcium phosphate, sintered and non-sintered ceramic particles, and combinations of such materials. If other such substances have therapeutic value in the orthopaedic field, it is anticipated that at least some of these substances will have use in the present invention, and such substances should be included in the meaning of "biocompatible inorganic material" and "biocompatible inorganic materials" unless expressly limited otherwise.

It is expected that various combinations of bioactive agents, biologically derived agents, cells, biological lubricants, biocompatible inorganic materials, biocompatible polymers can be used with the scaffolds and methods of the present invention.

It is expected that standard disinfection and sterilization techniques may be used with the products of the present invention.

EXAMPLE 1

A meniscus is prepared as shown in FIG. 1. An SIS device as shown in FIG. 8 is inserted into the space created by the meniscectomy and secured by suturing with 5-0 nylon sutures to the surrounding meniscal tissue. The incisions are closed and 2 ml of a solution of 1% sodium hyaluronate, of molecular weight between 2.4 and 3.6 million Daltons (the commercially-available ARTHREASE™ high molecular weight sodium hyaluronate) is injected into the knee joint cavity adjacent to the SIS device. After 3 weeks, 95% or more regeneration of the meniscal defect was seen in two out of three dogs. Moreover, the cartilage is mature and is similar in appearance to natural tissue.

In contrast, use of ARTHREASE™ injections alone, without the SIS implant, resulted in no tissue regeneration within the meniscal defect in three out of three dogs. Use of an SIS implant alone, without ARTHREASE™ injections, resulted in approximately 80% tissue regeneration in one dog and less than 50% regeneration in two of three dogs in this group.

EXAMPLE 2

A meniscus is prepared and a device inserted, as in Example 1. The incision is closed and HA (the commercially-available ARTHREASE™ high molecular weight sodium hyaluronate of EXAMPLE 1) is injected as in Example 1. Additional injections are provided two weeks and four weeks post-op. It is understood that other protocols for a series of injections may be used.

EXAMPLE 3

A meniscus is prepared as in Example 1. An SIS device as shown in FIG. 8 is placed in an HA solution (the commercially-available ARTHREASE™ high molecular weight sodium hyaluronate of EXAMPLE 1), and the HA is allowed to saturate the device. The device is then inserted, as discussed in Example 1. Optional additional injections are provided two weeks and four weeks post-op.

EXAMPLE 4

A meniscus is prepared as in Example 1. An SIS device as shown in FIG. 8 is obtained, wherein the device had been saturated in HA (the commercially-available ARTHREASE high molecular weight sodium hyaluronate of EXAMPLE 1) and lyophilized prior to packaging. The device is rehydrated in sterile saline or water and implanted as in Example 1.

Some commercial sodium hyaluronate solutions have a higher concentration of sodium hyaluronate. For example, Pharmacia Corporation of Peapack, N.J. identifies three different concentrations of sodium hyaluronate in its HEA-LON® line of products: 1% sodium hyaluronate, 1.4% sodium hyaluronate and 2.3% sodium hyaluronate for ophthalmologic use.

EXAMPLE 5

A cartilage defect is repaired with a device as shown in FIG. 11. HA is applied post-operatively to the repaired defect. When compared to cartilage defects repaired without HA, the repaired tissue is expected to be more mature, with a whiter, more hyaline-like appearance. Also, it is expected that the repaired tissue that is treated with a combination device and HA will show evidence of less severe degradative changes than is seen in the non-HA treated animals.

Although the examples all relate to use of HA salts, it is expected that other biological lubricants will provide similar benefits. It should be understood that the nature of the biological lubricant and the means of administering the biological lubricant can affect the quality of lubrication provided and can also affect the biological effects observed. For example, although a biological lubricant such as HA can be crosslinked to the matrix and still provide adequate lubrication, some GAG sulfates (e.g. chondroitin sulfate) can be expected to be less effective, or ineffective, as a lubricant if crosslinked or co-lyophilized with the underlying matrix, yet still be used for its biological effects. For some biological lubricants, it will be desirable to provide the biological lubricant in a fluidized form to maximize lubrication. In addition, different materials identified as falling within the definition of biological lubricants can be expected to have different efficacies as lubricants and different biological efficacies. Of the identified biological lubricants, those sharing properties (e.g. viscosity) similar to those of HA may provide greater clinical benefit as lubricants. Of the identified biological lubricants, those decreasing the coefficient of friction between the implant and healthy cartilage, compared to the case without the lubricant, are expected to be beneficial, and particularly those biological lubricants providing a reduced coefficient of friction for an extended period time. Other of the identified biological lubricants may provide greater clinical benefit as biologic agents. It should also be understood that materials identified as biological lubricants and the means of administering the material may be combined in various ways to take advantage of the properties of each and to maximize the clinical benefits of administering the various materials.

Although the invention has been described in detail with reference to certain preferred embodiments, variations and modifications exist within the scope and spirit of the invention as described and defined in the following claims.

The invention claimed is:
1. A cartilage repair device comprising
   a plug configured to be positioned in an opening formed in damaged hyaline cartilage, the plug being formed from an extracellular matrix selected from the group consisting of vertebrate small intestine submucosa, vertebrate liver basement membrane, vertebrate bladder submucosa, vertebrate stomach submucosa, vertebrate alimentary tissue, vertebrate respiratory tissue, and vertebrate genital tissue,
   an exogenous biological lubricant applied to the extracellular matrix, wherein the biological lubricant is crosslinked onto the extracellular matrix, and
   an anchor secured to the plug, the anchor including a head, an elongated central body extending from the head, and at least one barb extending from the elongated central body for engagement with bone,
   wherein the extracellular matrix possesses sufficient compressive strength and sufficient shear strength to withstand the loads applied to hyaline cartilage when the plug is positioned in the opening formed in damaged hyaline cartilage.

* * * * *